United States Patent [19]
Shibata et al.

[11] Patent Number: 6,091,075
[45] Date of Patent: Jul. 18, 2000

[54] AUTOMATIC FOCUS DETECTION METHOD, AUTOMATIC FOCUS DETECTION APPARATUS, AND INSPECTION APPARATUS

[75] Inventors: Yukihiro Shibata, Fujisawa; Shunji Maeda, Yokohama; Hiroshi Makihara, Yokohama; Minoru Yoshida, Yokohama; Yasuhiko Nakayama, Yokohama; Kenji Oka, Yokohama, all of Japan

[73] Assignee: Hitachi, Ltd., Tokyo, Japan

[21] Appl. No.: 09/087,901

[22] Filed: Jun. 1, 1998

[30]     Foreign Application Priority Data

Jun. 4, 1997   [JP]   Japan .................................. 9-146151

[51] Int. Cl.[7] ........................... G01N 21/00; G01N 21/88
[52] U.S. Cl. .................................. 250/559.44; 356/237.1
[58] Field of Search ........................... 250/201.2–201.4, 250/201.6–201.8, 204, 216, 559.44, 559.45, 559.46; 357/237.1, 237.3, 237.4, 237.5, 239.3

[56] References Cited

U.S. PATENT DOCUMENTS

| | | | |
|---|---|---|---|
| 3,614,232 | 10/1971 | Mathisen | 356/239 |
| 3,970,845 | 7/1976 | Hollis et al. | 250/236 |
| 4,953,964 | 9/1990 | Anafi et al. | 250/201 |
| 5,235,400 | 8/1993 | Terasawa et al. | 356/237 |

*Primary Examiner*—Stephone B. Allen
*Attorney, Agent, or Firm*—Antonelli, Terry, Stout & Kraus, LLP

[57] ABSTRACT

An automatic focus detection method comprises the steps of: irradiating onto a single spot of a sample a plurality of beams of illuminating light transmitted and condensed through an objective lens in a symmetrically diagonal manner with respect to an optical axis of the objective lens; branching reflected light from the same spot of the illuminated sample after transmission through the objective lens, in directions of illumination symmetrical with respect to the optical axis so as to obtain a plurality of optical images; and causing a photoelectric conversion device to receive the branched optical images for conversion to an electric signal representing light intensity distribution of the images, whereby a defocus of the sample is detected based on a discrepancy between the optical axis and the center of the light intensity distribution.

42 Claims, 15 Drawing Sheets

CROSS SECTION A-A

FIG. 10A
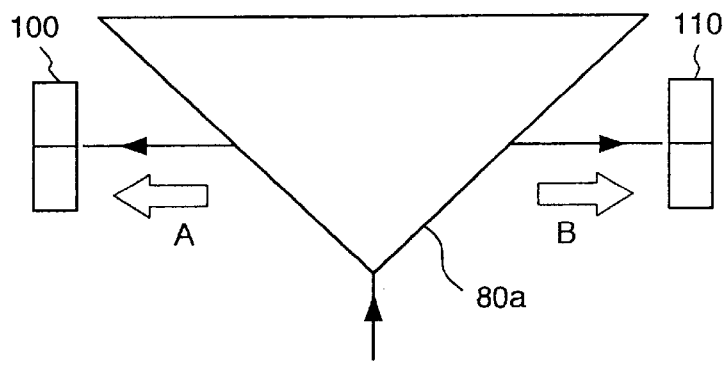
FIG. 10B
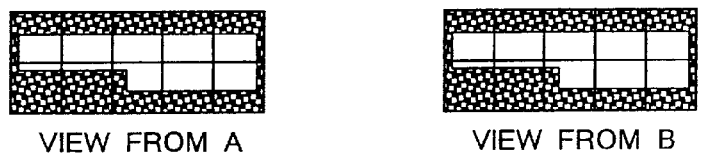
VIEW FROM A  VIEW FROM B
FIG. 10C
| $I\alpha 1$ | $I\alpha 3$ | $I\alpha 5$ | $I\alpha 7$ | $I\alpha 9$ |
|---|---|---|---|---|
| $I\alpha 2$ | $I\alpha 4$ | $I\alpha 6$ | $I\alpha 8$ | $I\alpha 10$ |
VIEW FROM A
| $I\beta 1$ | $I\beta 3$ | $I\beta 5$ | $I\beta 7$ | $I\beta 9$ |
|---|---|---|---|---|
| $I\beta 2$ | $I\beta 4$ | $I\beta 6$ | $I\beta 8$ | $I\beta 10$ |
VIEW FROM B
FIG. 10D
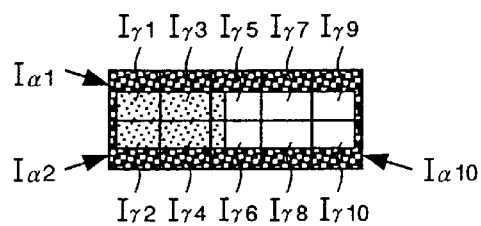

DIRECTION OF
FOCUS DETECTION

DIRECTION OF
FOCUS DETECTION

AUTOMATIC FOCUS DETECTION METHOD, AUTOMATIC FOCUS DETECTION APPARATUS, AND INSPECTION APPARATUS

BACKGROUND OF THE INVENTION

The present invention relates to an automatic focus detection method, an automatic focus detection apparatus and an inspection apparatus for optically examining any micro-pattern defects and infinitesimal foreign matters that may occur on wafers and reticules as well as on masks and substrates during the process of fabricating flat panel displays such as TFT displays.

Conventionally, micro-patterns formed on wafers and the like are visually inspected by microscope optics having object images detected, magnified, projected and suitably processed. With microscope optics, the depth of focus (DOF) on the side of the object is determined by the wavelength $\lambda$ of illuminating light and by the numerical aperture (NA) of an objective lens in use. If a sample is positioned outside the depth of focus, a defocused image is detected. The depth of focus (DOF) is defined by the expression (1) below.

$$DOF=\lambda/(2NA2) \quad (1)$$

One conventional technique for automatic focus detection whereby the surface of a sample is set to the focus of the objective lens is disclosed illustratively in Japanese Patent Laid-Open No. Hei 8-240765. One disadvantage of such a conventional technique is that a focus detection error is likely to occur due to changes in the reflectance of sample surfaces and in the density of patterns inspected.

Another disadvantage of the conventional focus detection method is that it tends to defocus in the presence of a stagger on the sample surface. That is, where the sample surface has a stagger that is included in the field, the detected focal point is given as a mean value between staggered surfaces. If the mean value exceeds a threshold depending on the stagger dimensions, the staggered surfaces of the sample are both outside the depth of focus DOF of the objective lens. The result is a defocused image. For example, the image of the object is focused correctly for depths of focus of up to about 0.3 $\mu$m. Beyond that depth, the image is liable to be defocused.

Today's need to speed up inspection tends to increase the length of a linear sensor used for image detection. With the linear sensor prolonged, however, the field of the automatic focus detection system is still limited. This makes it difficult to detect a true focal plane.

Where samples with diverse spectral reflectance characteristics are subject to automatic focus detection, conventional techniques require setting up a plurality of light sources for generating spectra that are different from one another. The requirement tends to enlarge necessary equipment and pushes up costs.

SUMMARY OF THE INVENTION

It is therefore an object of the present invention to provide an automatic focus detection method, an automatic focus detection apparatus and an inspection apparatus which will overcome the above and other deficiencies and disadvantages of the related art.

It is another object of the present invention to provide an automatic focus detection method and an automatic focus detection apparatus whereby focus detection errors caused by changes in the reflectance of sample surfaces are prevented to ensure normal focus detection.

It is a further object of the present invention to provide an automatic focus detection method and an automatic focus detection apparatus ensuring precise focus detection in the presence of staggers on the sample surface.

It is an even further object of the present invention to provide an inspection apparatus capable of inspecting with high resolving power any infinitesimal defects including tiny foreign matters in micro-patterns of samples such as semiconductor wafers during automatic focusing on their surface whose reflectance varies in a subtle manner.

In carrying out the invention and according to a first aspect thereof, there is provided an automatic focus detection method comprising the steps of: irradiating onto a single spot of a sample a plurality of beams of illuminating light transmitted and condensed through an objective lens in a symmetrically diagonal manner with respect to an optical axis of the objective lens; branching reflected light from the same spot of the illuminated sample after transmission through the objective lens, in the directions of the beams of illuminating light; irradiating an optical image formed by a branch of the reflected light onto a photoelectric conversion device for conversion to an electric signal representing intensity distribution of the irradiated optical image; and detecting a defocus of the sample based on a discrepancy between the optical axis and the center of the light intensity distribution on the photoelectric conversion device.

In a preferred structure according to the invention, the automatic focus detection method may further comprise the steps of: producing a mirror image of one optical image formed by one branch of the reflected light in inverse relation to another optical image formed by another branch of the reflected light; and composing the mirror image and the other optical image formed by the other branch of the reflected light so as to form a composite image which is irradiated onto the photoelectric conversion device.

In another preferred structure according to the invention, the automatic focus detection method may further comprise the step of irradiating each of a plurality of optical images formed by branches of the reflected light onto each of different photoelectric conversion devices.

According to a second aspect of the invention, there is provided an automatic focus detection apparatus comprising: illumination optics for irradiating onto a single spot of a sample a plurality of beams of illuminating light transmitted and condensed through an objective lens in a symmetrically diagonal manner with respect to an optical axis of the objective lens; and focus detection optics including a branching optical element for branching reflected light from the same spot of the illuminated sample after transmission through the objective lens, in directions of illumination symmetrical with respect to the optical axis so as to obtain a plurality of optical images; and a photoelectric conversion device for receiving the optical images from the branching optical element and converting the received images into signals representing light intensity distribution levels of the images.

In a preferred structure according to the invention, the photoelectric conversion device of the automatic focus detection apparatus may receive a composite image made of optical images which are branched by the branching optical element and are in inverse relation to one another, whereby a defocus on the sample is detected.

In another preferred structure according to the invention, each of optical images branched by the branching optical element may be irradiated onto each of different photoelectric conversion devices which in turn output signals. The output signals may be processed so as to detect a defocus of the sample.

In a further preferred structure according to the invention, the automatic focus detection apparatus may further comprise means for obtaining defocuses of the sample at a plurality of proximate points thereon. This arrangement permits detection of a stagger of sample surfaces.

According to a third aspect of the invention, there is provided an inspection apparatus comprising: illumination optics for illuminating a sample from above through an objective lens; branching optics for capturing through the objective lens reflected light from the sample under illumination by the illumination optics so as to branch the captured reflected light; image detection optics including a first photoelectric conversion device, the image detection optics forming a pattern image based on the branched reflected light from the branching optics, the pattern image being received by the first photoelectric conversion device for conversion into an image signal to be detected; focus detection optics including a branching optical element for branching the light branched by the branching optics, in directions of illumination symmetrical with respect to the optical axis of the illuminating light irradiated to the sample; and a second photoelectric conversion device for receiving an optical image based on the branched light from the branching optical element and converting the image into a focus detection signal to be output; and a processing circuit for processing the output of the second photoelectric conversion device. Preferably, the illumination optics of the inspection apparatus may include a first illuminating path for permitting transmission of the illuminating light for image detection having a first wavelength; a second illuminating path for permitting transmission of the illuminating light for focus detection having a second wavelength; and composing means for composing the illuminating light for image detection and the illuminating light for focus detection. Alternatively, the illumination optics may include ultraviolet light illumination optics for emitting ultraviolet light for image detection; visible light illumination optics for emitting visible light for focus detection; and composing means for composing the ultraviolet light and the visible light.

In another preferred structure according to the invention, the illumination optics of the inspection apparatus may include a stop whereby the illuminating light for focus detection is irradiated as a slit-like beam of light onto the sample. The objective lens may illustratively be made of a lens corrected substantially at infinity, with the branching optical element constituted by a knife-edge type mirror interposed between the objective lens and the composition optics.

In a further preferred structure according to the invention, the illumination optics of the inspection apparatus may include means for irradiating onto the sample ring-like illuminating light as the illuminating light for image detection.

In a still further preferred structure according to the invention, the illumination optics may include an aperture stop positioned in conjugate relation to a Fourier transformation plane of the objective lens, the aperture stop being varied with changes in the pupil diameter of the objective lens. Illustratively, incoherent light may be used as the illuminating light of the illumination optics.

Furthermore, the illumination optics of the inventive inspection apparatus may preferably include a field stop whereby the illuminating light for focus detection is projected as a slit-like beam of light onto the sample, the length of the projected slit-like spot on the sample being substantially the same as the size of a field detected by the image detection optics.

These and other objects, features and advantages of the invention will be apparent from the following more particular description of preferred embodiments of the invention, as illustrated in the accompanying drawings.

BRIEF DESCRIPTION OF THE DRAWINGS

FIG. 10A is a schematic view of focus detection optics;

FIGS. 10B through 10D are views indicating intensity levels of light intercepted by photoelectric conversion devices;

DESCRIPTION OF THE PREFERRED EMBODIMENTS

A first operating principle of the method and apparatus for automatic focus detection method according to the invention will now be described with reference to FIG. 1. Whereas the preferred focus detection method of the invention involves the use of overhead illumination optics, a method based on transmissive illumination will be explained below for purpose of simplification and illustration.

Figure 1A:
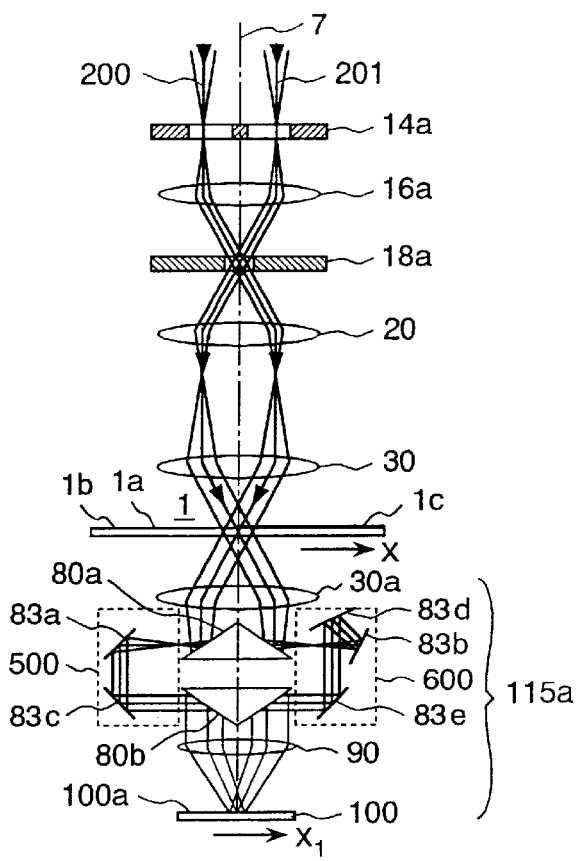
FIG. 1A is a schematic view illustrating the operating principle of an automatic focus detection apparatus embodying the invention.
Figure 1B:
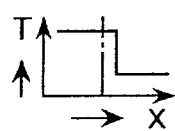
FIG. 1B is a graphic representation depicting a typical intensity distribution characteristic of light transmitted past a sample.
Figure 1C:
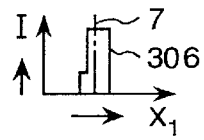
FIGS. 1C through 1E are graphic representations showing characteristics of output currents from a light detection unit.
Figure 1D:
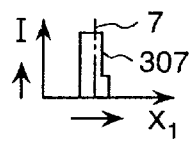
Figure 1E:
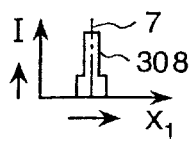

FIG. 1A illustrates schematically the operating principle of an automatic focus detection apparatus embodying the invention. FIG. 1B graphically depicts a typical intensity distribution characteristic of light transmitted through a sample. FIGS. 1C through 1E are graphic representations showing characteristics of output currents from a light detection unit. In FIG. 1B, the axis of abscissa represents a direction X on a sample, and the axis of ordinate denotes light intensity distribution T. In FIGS. 1C through 1E, the axis of abscissa stands for positions X1 on a photoelectric conversion device, and the axis of ordinate for output currents I representing the light intensity distribution on the photoelectric conversion device.

In FIG. 1A, the surface 1a of a sample 1 is divided into a high transmittance region 1b and a low transmittance region 1c. Where the setup of FIG. 1A is regarded as overhead illumination optics, the high transmittance region 1b and low transmittance region 1c represent a high reflectance region 1b and a low reflectance region 1c respectively. An apreture stop 14a is designed to form ring-like illumination as a secondary light source constituted by a large number of virtual point light sources. As such, the aperture stop 14a usually has a slit-like opening whose size and shape are made adjustable to provide different kinds of ring-like illumination. Alternatively, a plurality of removable aperture stops 14a may be prepared and any one of them may be selected for use. In FIG. 1A, light 200 transmitted on the left hand of an optical axis 7 of the aperture stop 14a passes through a lens 16a and a field stop 18a. It is assumed that the center of the field stop 18a coincides with the optical axis 7 and that the light having passed through the field stop 18a is uniform in intensity. The light 200 illuminates the sample 1 through a lens 20 and an objective lens 30. The sample 1 is shifted in the illustrated direction X, with a sample surface 1a at the focal point of focus detection optics 115a. The light 200 illuminating the sample surface 1a spans the high transmittance region 1b and low transmittance region 1c. If the boundary between the two regions 1b and 1c is dislodged slightly in the X direction, the intensity T of the light transmitted through the sample 1 takes on a distribution characteristic reflecting the staggered transmittance of the sample surface 1a as shown in FIG. 1B. That is, the light intensity loses its uniformity.

The light 200 transmitted through the sample 1 enters an objective lens 30a and is led into a branched optical path 500 after being reflected leftward by a knife-edge type mirror 80a. If the opening of the field stop 18a in the branching direction is relatively small and if the objective lens 30a is a lens corrected at infinity, the knife-edge type mirror 80a may be positioned so that a knife-edge vertex will coincide with the optical axis in the optical path between the objective lens 30a and an imaging lens 90. This arrangement will bisect the sample surface 1a in the illuminating direction. It follows that there is no need to position the knife-edge type mirror 80a in the exit pupil of the objective lens 30a. The light, arriving at the branched optical path 500 after reflection by the mirror 80a, is reflected by two mirrors 83a and 83c before being reflected by another knife-edgetype mirror 80b. The reflected light from the mirror 80c enters the imaging lens 90, forming an image of the sample surface 1a on a photoelectric conversion device 100. The light intensity distribution of this image is proportional to an output current from the photoelectric conversion device 100a. As shown in FIG. 1C, the light intensity takes on an asymmetrical characteristic 306 reflecting the transmittance distribution of the sample surface 1a. When the distribution characteristic 306 is used as a basis for detecting the height of the sample surface 1a, a height detection error results from the asymmetry of the image and detracts from the accuracy in detecting surface height. Meanwhile, light 201 transmitted on the right hand of the optical axis 7 of the aperture stop 14a illuminates the sample surface 1a symmetrically with respect to the light 200. The transmitted light enters the objective lens 30a and is led to a branched optical path 600 by reflection on the knife-edge type mirror 80a. The light from the mirror 80a is reflected by three mirrors 83b, 83d and 83e located in the optical path before being further reflected by the knife-edge type mirror 80b. The reflected light enters the imaging lens 90, forming an image of the sample surface 1a on the light-intecepting plane 100a of the photoelectric conversion device 100a. As mentioned, after being branched by the knife-edge type mirror 80a, the image formed by the light 201 is reflected by the three mirrors 83a, 83d and 83e before returning to the knife-edge mirror 80b for optical confluence. That is, the number of times the light 201 is reflected is one time less than the number of times the light 200 is reflected, i.e., by the mirrors 83a and 83c. This causes the image formed by the light 201 to be inverted with respect to the image formed by the light 200, with the inverted mirror image taking on a distribution characteristic 307 shown in FIG. 1D. That is, rendering the number of mirrors in the optical path 500 different from the number of mirrors in the optical path 600 by an odd number makes it possible to invert the image formed by the light 201 with respect to the image made by the light 200. Both the mirror image formed through inversion by the knife-edge type mirror 80b and imaging lens 90 and the image formed by the light 200 are subjected to composition.

Figure 6A:
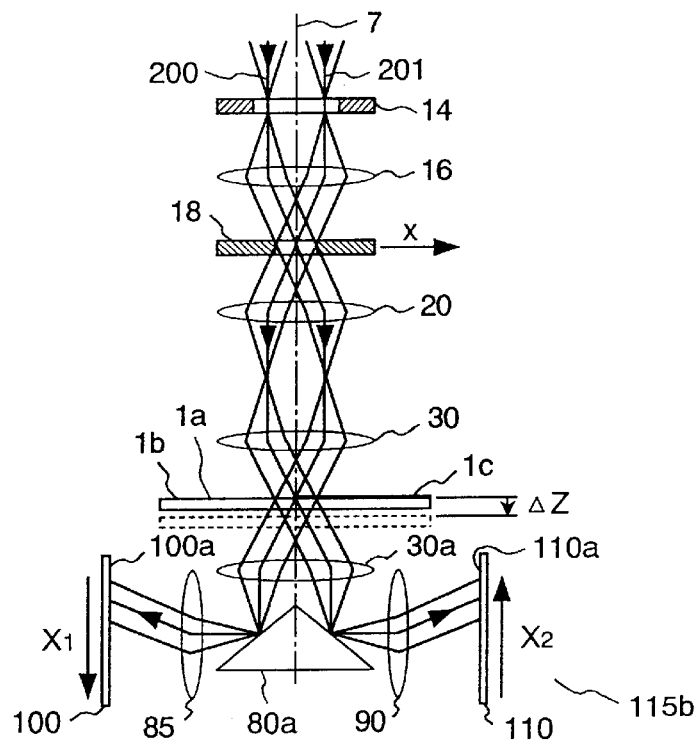
FIG. 6A is a schematic view depicting the operating principle of the focus detection apparatus of FIG. 5.
Figure 6B:
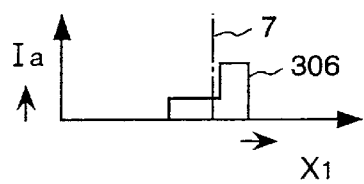
FIGS. 6B through 6G are graphic representations of characteristics for explaining the workings of the apparatus in FIG. 6A.
Figure 6E:
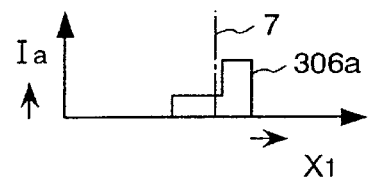

The two images formed by the light 200 and light 201 are composed into a composite image having a symmetrical distribution characteristic 308 shown in FIG. 6E. The arrangement prevents height detection error stemming from the asymmetrical image distribution. This effect is realized, as mentioned above, by simply rendering the number of plane mirrors (83a, 83c) in one optical path (500) different from the number of planetmirrors (83b, 83d, 83e) in the other optical path (600) by an odd number. FIG. 1A indicates that the sample surface 1a is position ed at the focal point of the optics. If the sample surface 1a is defocused, the composite image formed by the two kinds of light 200 and 201 as shown in FIG. 1E is dislodged in the same direction X1 at an imaging position of the photoelectric conversion device 100a. As a result, the distribution characteristic 308 of the composite image formed at the imaging position has its center position 7 varied with the height of the sample surface 1a. The perceived correlation between the center position and the sample surface height allows the defocus to be detected. It should be noted that the optics in which a defocused sample surface 1a causes the distribution characteristics 306 and 307 to shift in the same direction must be optics utilizing overhead illumination. For purpose of simplification and illustration, the setup of FIG. 1 is composed of optics of transmissive illumination, which is to be replaced by overhead illumination optics shown in FIG. 2.

Figure 2:
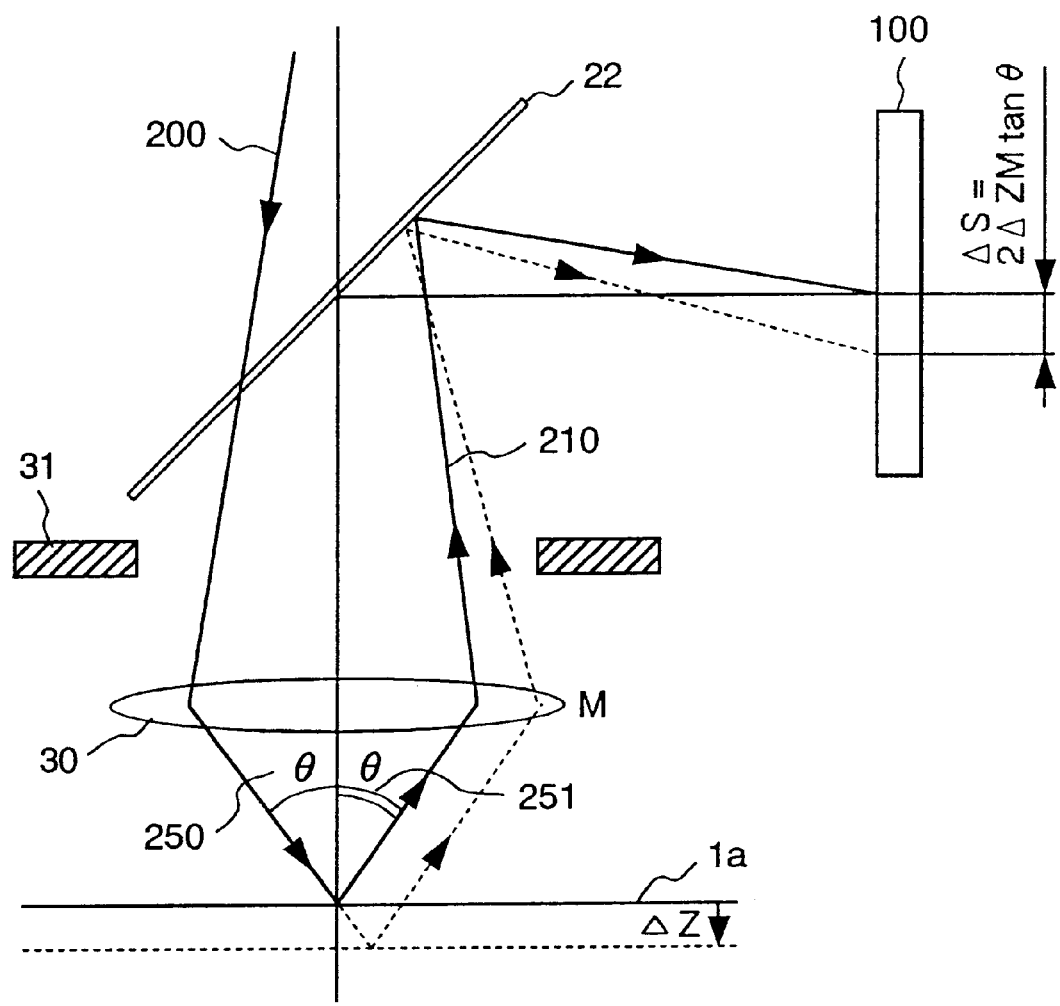
FIG. 2 is a schematic view sketching the operating principle of focus detection by use of overhead illumination.

FIG. 2 is a schematic view sketching the operating principle of focus detection by use of overhead illumination. As illustrated in FIG. 2, a light beam 200 enters the objective lens 30 and is condensed thereby onto the sample surface 1a from above. In this example, the angle of incidence 250 and the angle of reflection 251 are the same angle θ. A light beam 210 reflected by the sample surface is again reflected by light branching means 22 to form an image on a light-intercepting plane of the photoelectric conversion device 100. If M is assumed to denote the magnifying power of the objective lens 30 and if the sample surface 1a is lowered by ΔZ, the image formed on the light-intercepting plane is dislodged by 2ΔZMtanθ, which represents a function of the height ΔZ of the sample surface 1a. With that relationship in effect, the drop ΔZ of the sample surface 1a causes the composite image of FIG. 1E detected by the photoelectric conversion device 100, i.e., the center of the composite distribution characteristic 308, to shift from the optical axis 7 by 2ΔZMtanθ. Thus the defocus distance ΔS is equal to 2ΔZMtanθ, defined as a function of the height of the sample surface 1a. It follows that once the center of the composite distribution characteristic 308 is detected, the height ΔZ of the sample surface 1a is also recognized.

From the objective lens 30 in FIG. 1A, primarily two kinds of illuminating light 200 and 201 are irradiated to the surface 1a of the sample 1. When the two light beams 200 and 201 are irradiated in a diagonally symmetrical manner with respect to the optical axis, the transmitted light of the respective beams is branched by the knife-edge type mirror 80a. The number of mirrors 83 in the optical path 500 is made different from the number of mirrors 83 in the optical path 600 by an odd number. This arrangement inverts the image formed by the light 201 with respect to the image formed by the light 200. The inverted mirror image made from the light 201 by the knife-edge type mirror 80b and imaging lens 90 and the image from the light 200 are put together. The resulting composite image has the symmetrical distribution characteristic 308 shown in FIG. 1E, whereby the height detection error stemming from asymmetrical image distribution is prevented. When the defocus distance ΔS (=2ΔZMtanθ) of the composite distribution characteristic 308 relative to the optical axis 7 is detected, the height ΔZ of the sample surface 1a may be calculated. In turn, the calculated height ΔZ of the sample surface 1a may be used as a basis for implementing a focusing procedure, as will be described later.

Figure 3:
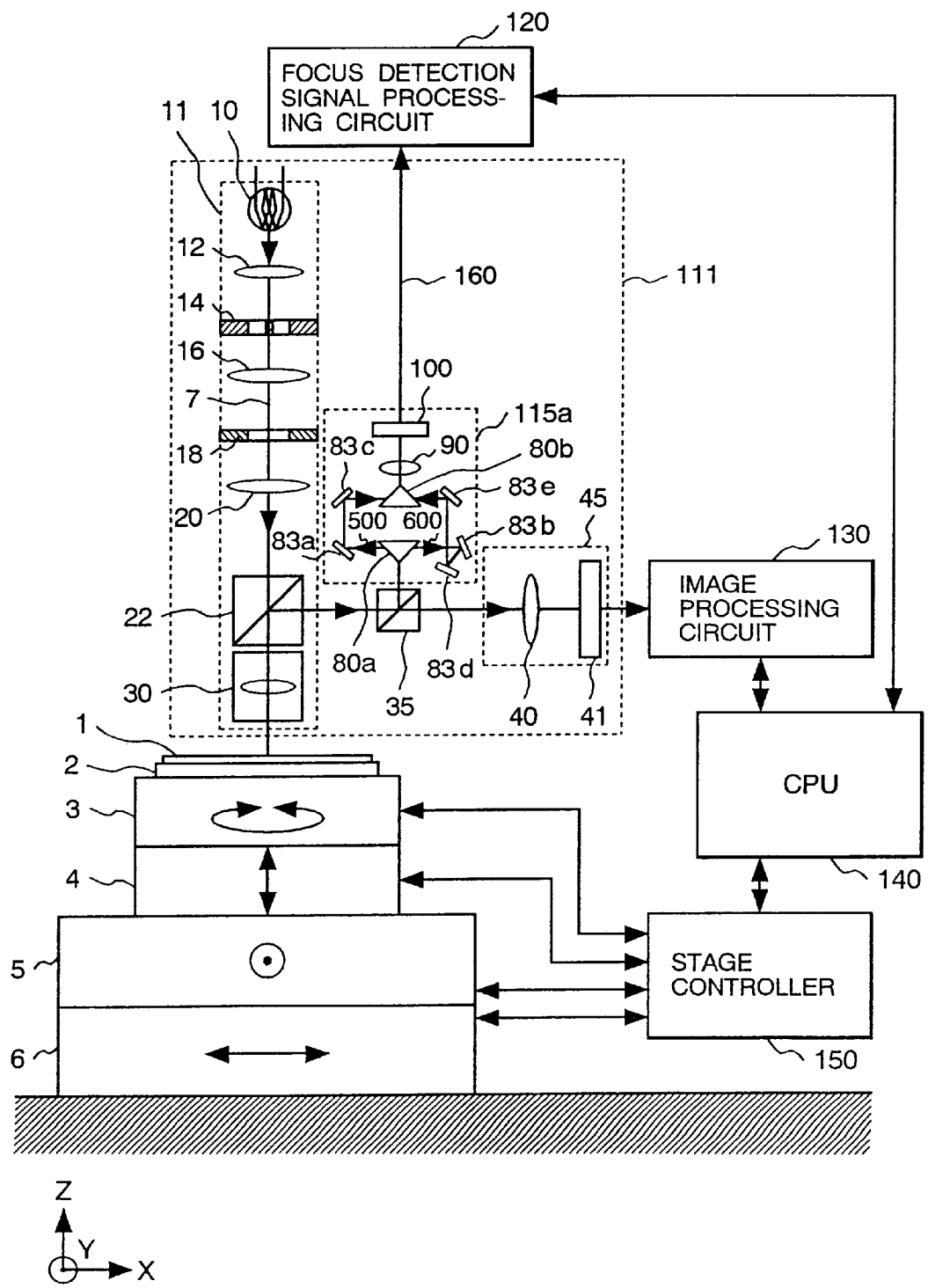
FIG. 3 is a schematic block diagram of a visual inspection apparatus incorporating a focus detection apparatus also embodying the invention.

Described below with reference to FIG. 3 is typical optical equipment for inspecting patterns, among others, on sample surfaces by use of the inventive method and optics for focus detection. More specifically, FIG. 3 is a schematic block diagram of a visual inspection apparatus incorporating a focus detection apparatus embodying the invention. In FIG. 3, a sample 1 is vacuum-gripped by a chuck 2. The chuck 2 is mounted on top of a rotational motion stage 3 for rotating the sample 1, a Z stage 4 for moving the sample 1 up and down as seen in the figure (in Z direction), a Y stage 5 for moving the sample 1 perpendicularly to the sheet carrying the view (in Y direction), and an X stage 6 for moving the sample 1 crosswise as seen (X direction). Optics 111 above the sample 1 is used to detect an optical image of the sample 1. The detected optical image is used as a basis for visually inspecting patterns that may be formed on the sample 1. The optics 111 is constituted primarily by illumination optics 11, image detection optics 45 for imaging the sample 1, and focus detection optics 115a.

A light source 10 in the illumination optics 11 is an incoherent light source such as a halogen lamp. Light emitted by the light source 10 passes through an opening of an aperture stop 14 having a slit-like orifice (i.e., a stop for forming ring-like illumination as a secondary light source made of a large number of virtual point light sources). The light is then transmitted through a lens 16 (e.g., collimator lens) to reach a field stop 18. The field stop 18 is a last-stage stop by which to form the ring-like illumination as the secondary light source composed of numerous virtual point light sources. Serving as it does, the field stop 18 generally has a slit type opening. The aperture stop 14 or field stop 18 is made adjustable in size and shape so that the light past the field stop 18 may emit different kinds of ring-like illumination. Alternatively, the aperture stop 14 or field stop 18 may each be selected from a plurality of removable stops prepared in advance. For example, the aperture stop 14 or field stop 18 may have a liquid crystal diaphragm, with the stop pattern changed automatically by switching signals applied to the liquid crystal. The arrangement allows the illuminating light of the image detection optics 45 to also serve as illuminating light of the focus detection optics 115. Alternatively, the illumination optics 11 may be switched as needed to an ordinary light source for illumination. The light from the secondary light source past the field stop 18 passes through the lens 20 (e.g., collimator lens) and light branching means 22 to enter the objective lens 30. From the objective lens 30, as shown in FIG. 1A, the light is irradiated in a substantially perpendicular direction to the sample 1 in a diagonally symmetrical manner with respect to the optical axis. The light branching means 22 may be implemented in the form of a half mirror or a polarized beam splitter. If a polarized beam splitter is adopted, a ¼ waveform plate or the like needs to be interposed between the splitter and the sample 1 so as to forestall a precipitous decline in the quantity of detected light. The illumination optics 11 and the image detection optics 45 are discussed in more specific terms in Japanese Patent Laid-Open No. Hei 8-162511.

The publication cited above discloses an apparatus wherein ring-like diffused illuminating light formed by numerous virtual point light sources 18 is polarized and transmitted through the pupil of the objective lens 30 for condensed illumination onto a pattern on the surface of the sample 1 (target object to be observed). First or second order diffracted light including zero order diffracted light reflected from the pattern on the sample 1 is condensed and transmitted through the pupil of the objective lens 30, whereby an image of the pattern on the sample 1 is obtained. The acquired image is input to a photoelectric conversion device 41 for conversion to an image signal representing the sample surface pattern.

The light that illuminated the sample 1 is reflected, scattered and diffracted thereby. The light falling within the numerical aperture (NA) enters again the objective lens 30. Past the objective lens 30, the light is reflected by the light branching means 22 and guided to the image detection optics 45 for forming an image of the sample 1 and to the focus detection optics 115a. The reflected light from the light branching means 22 enters another light branching means 35. After transmission through the light branching means 35, the transmitted light passes through an imaging lens 40 to form an image of a surface pattern of the sample 1 on the photoelectric conversion device 41. The light branching means 35 may be implemented illustratively in the form of a half mirror (T:R need not be 1:1), a dichroic mirror or a polarized beam splitter. The photoelectric conversion device 41 may be a photodiode, a linear sensor, a TDI sensor or a TV camera. The light reflected by the light branching means 35 is led to the focus detection optics 115a wherein the knife-edge type mirror 80a splits the light into two beams in the direction of the light illuminating the sample 1. The light of the branched optical path 500 is reflected by the mirrors 83a and 83c before reaching the knife-edge type mirror 80b. The light of the branched optical path 600 is reflected by the three mirrors 83*b*, 83*d* and 83*e* before arriving at the knife-edge type mirror 80*b* to converge on the light of the optical path 500. The converged light beams are composed by the imaging lens 90 into an image of the sample 1 on the photoelectric conversion device 100. Because the two images from the two optical paths are in mirror image relation to each other, the composite image takes on a symmetrical distribution characteristic if the sample 1 is located at the focal point of the objective lens 30. The photoelectric conversion device 100 may be a linear sensor, a TDI sensor or a photodiode. The field stop 18, the sample 1, the photoelectric conversion device 41 of the image detection optics 45, and the photoelectric conversion device 100 of the focus detection optics 115*a* are in image forming relation to one another, are optically conjugate.

A signal representing the distribution characteristic detected by the photoelectric conversion device 100 in the focus detection optics 115*a* is input to a focus detection signal processing circuit 120 via a cable 160. Given the signal, the processing circuit 120 detects a defocus distance ΔS between the height of the sample 1 and the focal point of the objective lens 30. The detected data denoting the defocus distance ΔS are sent to a CPU 140. The CPU 140 supplies a stage controller 150 with a command corresponding to the defocus distance ΔS; the command causes the stage controller 150 to drive the Z stage 4. More specifically, the stage controller 150 feeds necessary pulses to the Z stage 4 to move the sample 1 in the Z direction until the sample 1 reaches the focal point of the objective lens 30. This constitutes an automatic focusing function. The CPU 140 also inputs to an image processing circuit 130 an optical image signal representing brightness gradations of a circuit pattern formed on the sample 1, the pattern being imaged and detected by the photoelectric conversion device 41 of the image detection optics 45. The optical image signal is subjected to analog-to-digital conversion before undergoing such processes as shading correction, dark level correction and distorted image correction. The acquired image signal is compared with a reference image signal for alignment. Any image difference (i.e., image mismatch) that may result from the comparison is extracted and stored as a defect candidate. Defect candidates are examined minutely for microscopic defects including foreign matters on the basis of characteristic quantities such as the area, center of gravity and maximum length of the defect in question.

The sample 1 is moved two-dimensionally (i.e., in the X and Y directions) by the X stage 6 and Y stage 5. The rotational motion stage 3 is used to attain alignment between the moving direction of the X and Y stages 6 and 5 on the one hand and the rotation of the pattern formed on the sample 1 on the other hand.

Figure 4A:
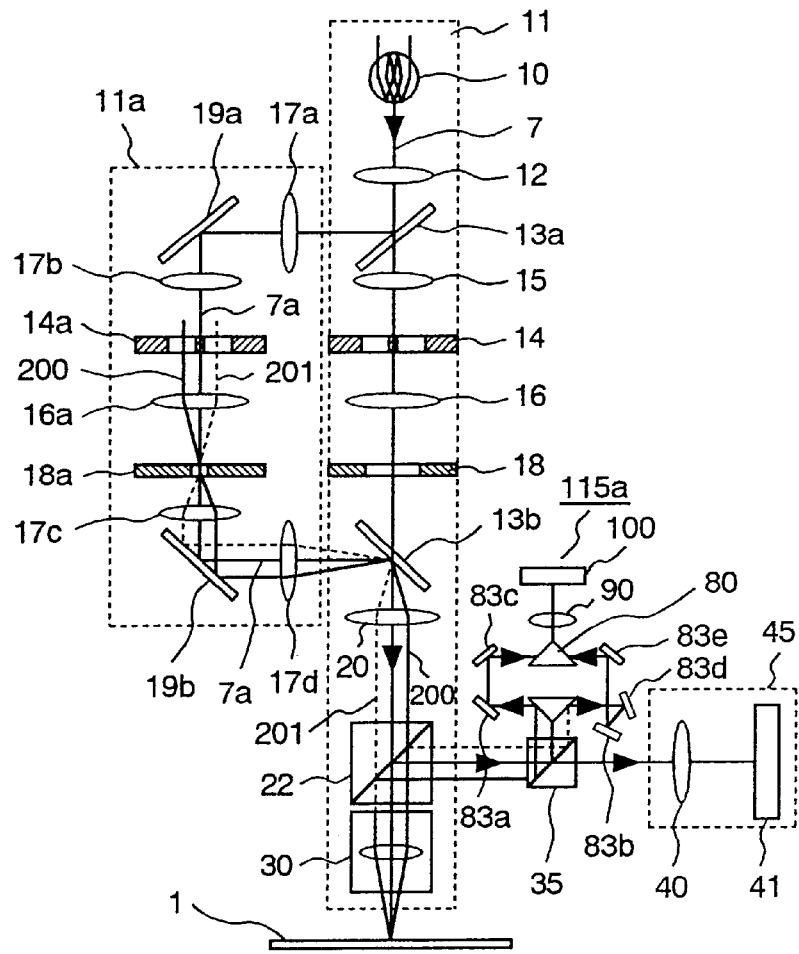
FIG. 4A is a schematic view of illumination optics also embodying the invention and used in the visual inspection apparatus of FIG. 3.
Figure 4B:
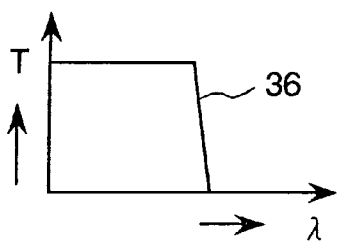
FIG. 4B is a graphic representation of characteristics for explaining the optics of FIG. 4A.

Described below with reference to FIGS. 4A and 4B is the setup wherein the illumination optics is divided into the image detection optics 45 and the focus detection optics 115*a*. FIG. 4A is a schematic view of illumination optics also embodying the invention and used in the visual inspection apparatus of FIG. 3. FIG. 4B is a graphic representation of characteristics for explaining the optics of FIG. 4A. In FIG. 4B, the axis of abscissa represents a wavelength λ of light and the axis of ordinate denotes transmittance T.

Figure 12A:
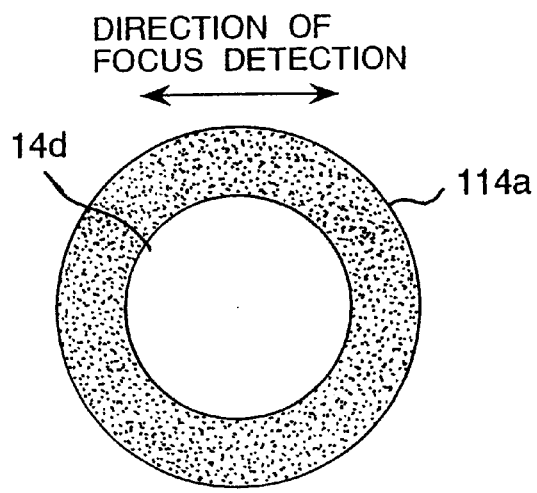
FIGS. 12A through 12D are plan views of aperture stops.
Figure 12B:
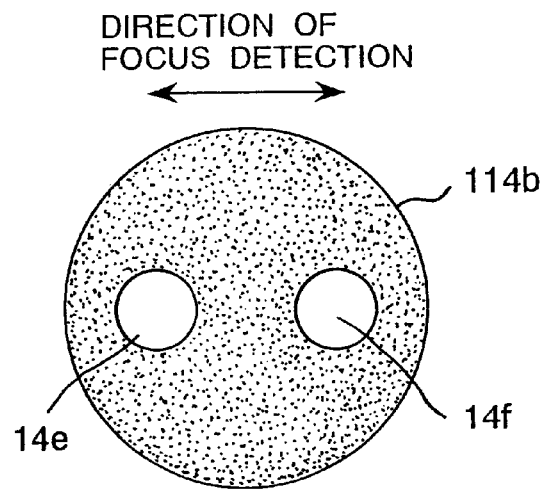
Figure 12C:
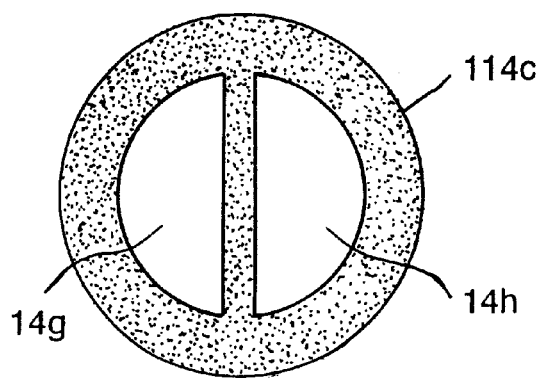
Figure 12D:
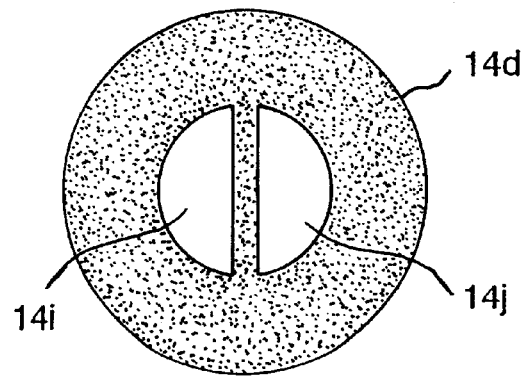
Figure 13A:
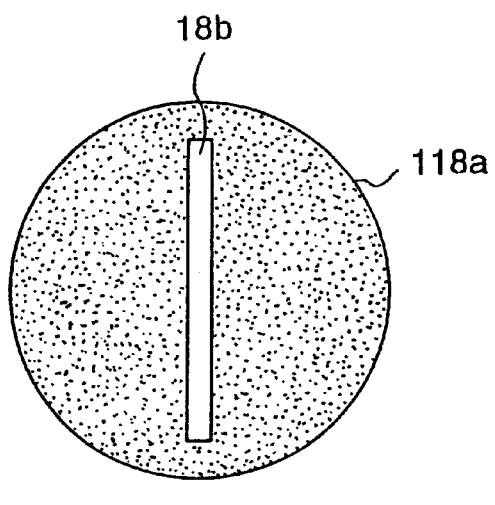
FIGS. 13A and 13B are plan views of field stops.
Figure 13B:
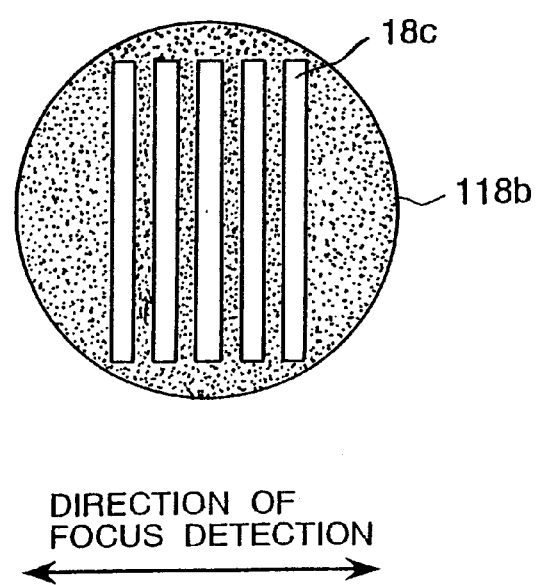

There are two reasons for bisecting the illumination optics. First, the field stop 18*a* for producing illuminating light for focus detection is required to have either an extremely small spot opening or a very narrow slot opening as shown in FIG. 13, either opening being conducive to averting effects of any stagger on the sample surface 1*a* at least in the direction of focus detection. Second, the aperture stop 14*a* for producing illuminating light for focus detection needs to be devised so as to make either a ring-like light beam symmetrical with respect to the optical axis as shown in FIG. 12A, or two light beams as illustrated in FIGS. 12B, 12C and 12D. Where ring-type illumination optics is used, the aperture stop 14*a* produces a ring-like light beam symmetrical with respect to the optical axis. This means that if the round opening of the field stop 18*a* is made sufficiently large, the illuminating light may be shared by both image detection and focus detection systems. In that case, however, it is necessary to have two units of illumination optics installed separately or in parallel for image detection and focus detection, as shown in FIG. 4A. The setup is needed so that the field stop 18*a* for emitting focus detecting light may either have a spot opening small enough to avert effects of staggers on the sample surface 1*a* at least in the focus detection direction, or have an extremely narrow slit opening as shown in FIG. 13A or 13B. Light emitted by the light source 10 passes through a lens 12 and is split by a dichroic mirror 13*a* into transmitted light on the one hand and reflected light on the other hand depending on the wavelength. The transmitted light serves as illuminating light of the image detection optics 45 (i.e., image detecting light) and the reflected light as illuminating light of the focus detection optics 115*a* (focus detecting light).

The dichroic mirror 13*a*, having a transmittance characteristic 36 illustrated in FIG. 4B, allows light with wavelengths of less than "a" to pass through and causes light with wavelengths of "a" or higher to be reflected. Light with different wavelengths may be transmitted if any one of different dichroic mirrors may be selected and installed. Illustratively, the optics of FIG. 4A may allow light with wavelengths of less than 600 nm to pass through and may cause light with wavelengths of 600 nm or higher to be reflected. The mirror for splitting light is not limited to the dichroic mirror 13*a*. An obvious alternative is the use of a half mirror arrangement having a plurality of optical paths equipped with filters to let pass light with wavelengths of specific wavelengths. The light reflected by the dichroic mirror 13*a* proceeds along an optical axis 7*a* of the focus detecting illumination optics 11*a*, to be reflected by a mirror 19*a* via a relay lens 17*a*. Past a lens 17*b*, the reflected light enters the aperture stop 14*a* for focus detection as shown in FIGS. 12A through 12D. The light beams 200 and 201 transmitted through the aperture stop 14*a* are condensed by the lens 16*a* for entry either into a very small spot (a small, round opening) or into the field stop 18*a* having a narrow-slit arrangement in the focus detection direction as shown in FIG. 13A or 13B. Past the field stop 18*a*, the illuminating light proceeds from a relay lens 17*c* to a mirror 19*b* to a relay lens 17*d*, and is reflected by a dichroic mirror 13*b*. The light from the illumination optics 11 and the light from the focus detecting illumination optics 11*a* are converged again by the mirror 13*b*.

Moving past the dichroic mirror 13*a*, the illuminating light for the image detection optics 45 (i.e, image detecting light) passes through a lens 15 and the aperture stop 14. The light transmitted past the aperture stop 14 is shaped illustratively into ring-like illuminating light. The ring-like illuminating light is condensed by the lens 16 for passage through the field stop 18 whereby the light is converted to ring-shaped illuminating light having illustratively a predetermined spot diameter. The light is emitted as a secondary light source.

The illuminating light for image detection and that for focus detection are forwarded through the lens 20 and transmitted through the light branching means 22 such as a half mirror or polarized beam splitter. The transmitted light passes through the objective lens 30 to illuminate the sample 1 in the form of light beams from the field stops 18 and 18a. The light reflected and diffracted by the sample 1 again enters the objective lens 30 and is reflected by the light branching means 22. Of the reflected light, that part of light for image detection past the dichroic mirror 35 forms an image of the sample 1 on the photoelectric conversion device 41 of the image detection optics 45. The light for focus detection reflected by the dichroic mirror 35 is guided to the focus detection optics 115a.

Figure 5:
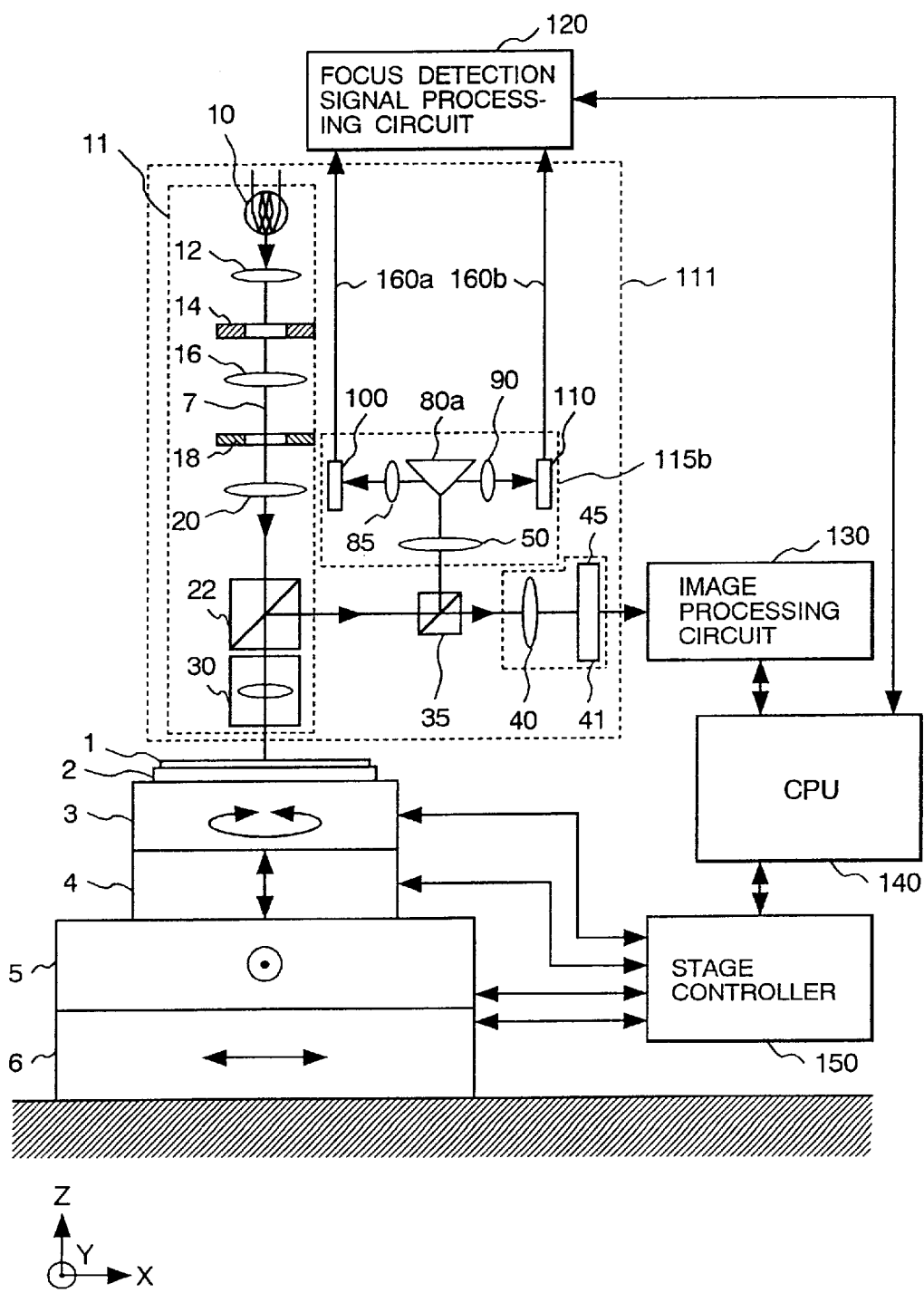
FIG. 5 is a schematic block diagram of a visual inspection apparatus incorporating another focus detection apparatus also embodying the invention.

Described below with reference to FIG. 5 is an inspection apparatus for inspecting patterns formed on samples by use of the focus detection method and focus detection optics according to the invention. FIG. 5 is a schematic block diagram of a visual inspection apparatus incorporating a focus detection apparatus also embodying the invention.

With the exception of the focus detection optics 115, the inspection apparatus of FIG. 5 is structurally the same as that of FIG. 3. In FIG. 5, the light that illuminated the sample 1 is reflected, scattered and diffracted thereby. The light falling within the numerical aperture (NA) enters again the objective lens 30. Past the objective lens 30, the light is reflected by the light branching means 22 and guided to the image detection optics 45 for forming an image of the sample 1 and to the focus detection optics 115b. The reflected light from the light branching means 22 enters the light branching means 35. After transmission through the light branching means 35, the transmitted light passes through the imaging lens 40 to form an image of a surface pattern of the sample 1 on the photoelectric conversion device 41. The light branching means 35 may be implemented illustratively in the form of a half mirror (T:R need not be 1:1), a dichroic mirror or a polarized beam splitter. The photoelectric conversion device 41 may be a photodiode, a linear sensor, a TDI sensor or a TV camera.

The light reflected by the light branching means 35 is led to the focus detection optics 115b wherein a lens 50 and the pupil of the objective lens 30 combine to produce an exactly or approximately conjugate position. In that position is installed the knife-edge type mirror 80a which splits light into two beams in the direction of the light illuminating the sample 1. The split beams form images of the sample 1 on photoelectric conversion devices 100 and 110 via imaging lenses 85 and 90 respectively. The photoelectric conversion devices 100 and 110 may be linear sensors, TDI sensors or photodiodes. The field stop 18, the sample 1 and the photoelectric conversion device 41 of the image detection optics 45 are in conjugate relation to one another, and so are the photoelectric conversion devices 100 and 110 of the focus detection optics 115b. In other words, the photoelectric conversion devices 41, 100 and 110 are optically conjugate. Signals representing the distribution characteristics detected by the photoelectric conversion devices 100 and 110 in the focus detection optics 115a are input to the focus detection signal processing circuit 120 via cables 160a and 160b. Given the signals, the processing circuit 120 detects a defocus distance between the height of the sample 1 and the focal point of the objective lens 30. The detected data denoting the defocus distance are sent to the CPU 140. The CPU 140 in turn supplies a stage controller 150 with a command corresponding to the defocus distance; the command causes the stage controller 150 to drive the Z stage 4. That is, the stage controller 150 feeds necessary pulses to the Z stage 4 to move it for automatic focusing. An optical image of the sample 1 detected by the photoelectric conversion device 41 of the image detection optics 45 is input to the image processing circuit 130 for image storage and defect checks. The sample 1 is moved in the X and Y directions (i.e., two-dimensionally) by the X stage 6 and Y stage 5.

The operating principle of the focus detection apparatus used by the inspection apparatus of FIG. 5 will now be described with reference to FIGS. 6A through 6G. Whereas the focus detection apparatus of FIG. 5 is shown employing overhead illumination optics, the optics of FIG. 6A uses transmissive illumination for purpose of simplification and illustration.

FIG. 6A is a schematic view depicting the operating principle of the focus detection apparatus of FIG. 5. FIGS. 6B through 6G are graphic representations of characteristics for explaining the workings of the apparatus in FIG. 6A. In FIG. 6A, the surface 1a of the sample 1 comprises a high transmittance region 1b and a low transmittance region 1c. Since the inspection apparatus of FIG. 5 adopts overhead illumination optics, the high transmittance region 1b and low transmittance region 1c in FIG. 6A correspond to the high reflectance region 1b and low reflectance region 1c in FIG. 5 respectively.

The light 200 transmitted on the left hand of the optical axis 7 of the aperture stop 14 passes through the lens 16 and then the field stop 18, i.e., a last-stage secondary light source forming ring-like illuminating light. It is assumed that the center of the field stop 18 as the secondary light source for emitting ring-like illuminating light coincides with the optical axis 7 and that the light having passed through the field stop 18 is uniform in intensity. The light 200 illuminates the sample 1 primarily in diagonal directions with respect to the optical axis via the lens 20 and objective lens 30. The sample surface 1a is assumed to be at the focal point of the focus detection optics 115b. If the light 200 illuminating the sample surface 1a spans the high transmittance region 1b and low transmittance region 1c, the transmitted light takes on a light intensity distribution characteristic representing the irregular transmissive state of the sample surface 1a. That is, the light intensity loses its uniformity. Transmitted through the sample surface 1a, the light 200 enters the objective lens 30a. Past the objective lens 30a, the light is reflected by the knife-edge type mirror 80a toward the photoelectric conversion device 100 to form on its light-intercepting plane 100a an image of the sample surface 1a via the imaging lens 85. If the opening of the field stop 18 in the branching direction is relatively small and if the objective lens 30a is a lens corrected at infinity, the knife-edge type mirror 80a may be positioned so that a knife-edge vertex will coincide with the optical axis in the optical path between the objective lens 30a and the imaging lens 85. This arrangement bisects the sample surface 1a in the illuminating direction. It follows that there is no need to position the knife-edge type mirror 80a in the exit pupil of the objective lens 30a. The light intensity distribution of the image formed on the light-intercepting plane 100a of the photoelectric conversion device 100, i.e., sensor output current distribution, becomes asymmetrical reflecting the transmittance distribution of the sample surface 1a, as indicated by a characteristic line 306 in FIG. 6B. FIG. 6A indicates that the direction X of the field stop 18 turns into a direction X1 for the photoelectric conversion device 100 and into a direction X2 for the focus detection sensor 110. In FIG. 6B, the axis of abscissa stands for positions in the direction X1 on the photoelectric conversion device 100, and the axis of ordinate represents an output current Ia from the device 100 representing the light intensity distribution on the device 100.

Likewise, the light 201 transmitted on the right hand of the optical axis 7 of the aperture stop 14 illuminates the sample surface 1a through the objective lens 30. The light 201 emitted to the sample surface 1a is symmetrical about the optical axis with respect to the light 200 described above. The light is transmitted through the sample surface 1a, enters the objective lens 30a and is reflected by the knife-edge typemirror 80a toward the photoelectric conversion device 110. Through the imaging lens 90, the light forms an image of the sample surface 1a on the light-intercepting plane 110a of the photoelectric conversion device 110.

Figure 6C:
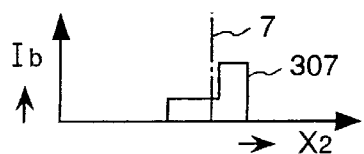

The light intensity distribution of the image formed on the light-intercepting plane 110a of the photoelectric conversion device 110 corresponds to the output current distribution of the device 110, shown as a distribution characteristic 307 in FIG. 6C. The characteristic 307 is asymmetrical as it reflects the transmittance distribution of the sample surface 1a. In FIG. 6C, the axis of abscissa stands for positions in the direction X2 on the photoelectric conversion device 110, and the axis of ordinate represents an output current Ib from the device 110 representing the light intensity distribution on the device 110.

If the sample surface 1a is at the focal point of the focus detection optics 115b, the distribution characteristic 306 detected by the photoelectric conversion device 100 coincides with the distribution characteristic 307 perceived by the focus detection sensor 110. In that case, as shown in FIG. 6D, the distribution characteristics 306 and 307 added up symmetrically about the reference optical axis 7 produce a composite distribution characteristic 308 having a waveform that is symmetrical about the optical axis. This ensures highly precise focus detection, with no focus detection error dependent on the transmittance distribution of the sample surface 1a. In FIG. 6D, the axis of ordinate denotes a current Iab adding up the currents Ia and Ib.

Figure 6F:
Figure 6D:
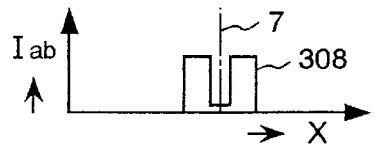
Figure 6G:
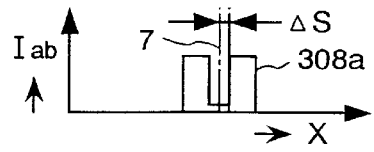

In FIG. 6A, when the sample surface 1a is lowered by ΔZ, the images of the surface 1 are shifted, accompanied by corresponding changes of distribution characteristics 306a and 307a as shown in FIGS. 6E and 6F. The distribution changes reflect deviations in the light intensity distribution detected by the photoelectric conversion devices 100 and 110 in the framework of the relations illustrated in FIG. 2. Although the optics in which the drop ΔZ of the sample surface 1a entails the shifts of the distribution characteristics 306a and 307a corresponding to the altered light intensity distribution needs to be overhead illumination optics, FIG. 6A shows a transmissive illumination setup for purpose of simplification and illustration. The distribution characteristics 306a and 307a detected respectively by the photoelectric conversion devices 100 and 110 are added up symmetrically about the optical axis 7 to produce a composite distribution characteristic 308a shown in FIG. 6G. The center of the composite distribution characteristic 308a is dislodged from the optical axis 7 (i.e., defocused). The defocus distance ΔS is given as 2ΔZMtanθ representing a function of the height of the sample surface 1a. When the defocus distance ΔS of the composite distribution characteristic 308a is detected with respect to the optical axis 7, the height ΔZ of the sample surface 1a may be detected. That is, the defocus distance between an object and the focus of the optics on the object side is detected. If the sample surface 1a is not at the focal point of the focus detection optics 115b, there will be no symmetry in the composite distribution characteristic 308a combining the characteristics detected by the two photoelectric conversion devices 100 and 110 acting as opticalsensors. As long as the sample surface 1a is at the focal point of the focus detection optics 115b, there always occurs a symmetrical distribution characteristic 308a with no focus detection error dependent on the transmittance distribution of the sample surface 1a. Although FIG. 6A shows transmissive illumination optics for ease of understanding, the setup must be replaced by overhead illumination optics which alone possesses focus detection sensitivity to embody the invention as illustrated in FIG. 5. In the manner described above, the composite distribution characteristic 308a becomes symmetrical as shown in FIG. 6G. This prevents sample surface height detection errors stemming from asymmetrical image distribution. When the defocus distance ΔS (=2ΔZMtanθ) of the composite distribution characteristic 308a is detected with respect to the optical axis 7, the height ΔZ of the surface 1a is calculated. The computed height ΔZ of the sample surface 1a is transmitted by the CPU 140 to the stage controller 150 for control over the Z stage 4, whereby focusing is implemented.

Figure 7A:
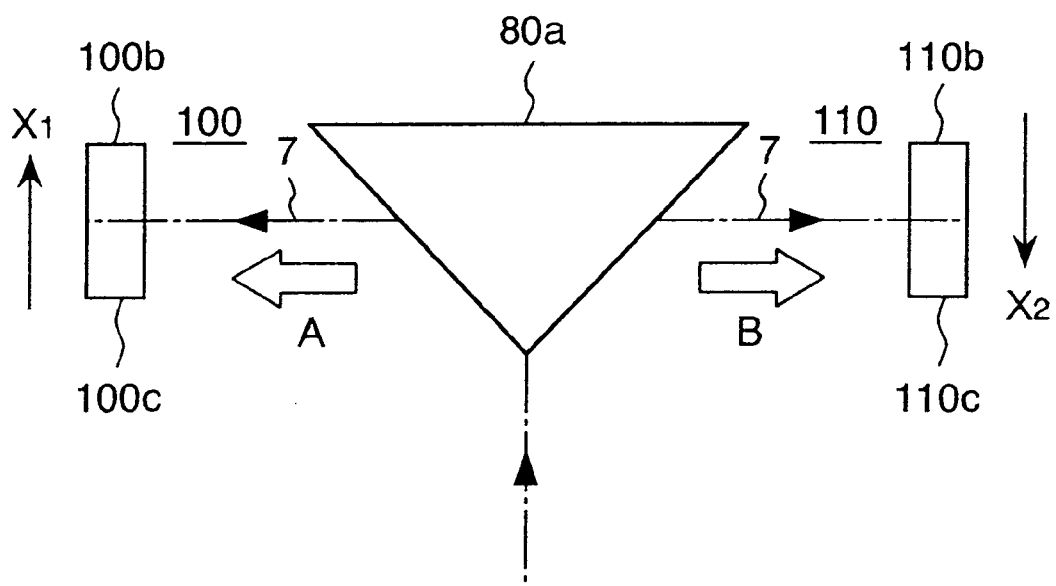
FIG. 7A is a schematic view of focus detection optics also embodying the invention.
Figure 7B:
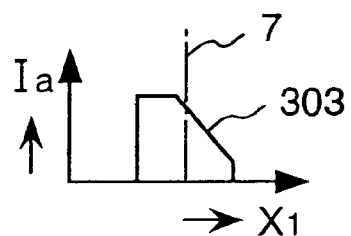
FIGS. 7B and 7C are graphic representations of characteristics for explaining the focus detection optics of FIG. 7A.
Figure 7C:
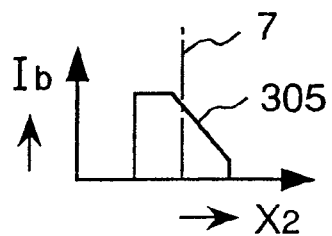

Described below with reference to FIGS. 7A through 7C is a focus detection apparatus embodying the invention by use of a bisected photodiode arrangement as photoelectric conversion devices, the focus detection apparatus being incorporated in the inspection apparatus of FIG. 5.

FIG. 7A is a schematic view of focus detection optics embodying the invention. In FIG. 7A, the photoelectric conversion devices 100 and 110 of the focus detection optics 115b are a focus detecting photodiode each. The focus detecting photodiode 100 is bisected into photodiodes 100b and 100c as illustrated. The boundary between the two photodiodes 100b and 100c coincides with the optical axis 7. Likewise, the focus detecting diode 110 is bisected into photodiodes 110b and 110c, with the boundary therebetween coinciding with the optical axis 7. The setup is devised so as to enable focus detection. If the sample 1 has a uniform reflectance and if the sample 1 is at the focal point of the focus detection optics 115b, the quantity of light received by each of the two photodiodes 100b and 100c is the same. A theoretical focal point z is given by the following expression (2):

$$z = (Ia1 - Ia2)/(Ia1 + Ia2) \quad (2)$$

where Ia1 and Ia2 represent output currents of the photodiode 100b and 110c respectively. If the sample 1 is exactly at the focal point, the value z is 0 in the expression (2).

If there is no denominator in the expression (2), the function involving both the focal point z and the stagger ΔZ of the sample 1 will vary. That can be prevented by inserting a suitable denominator in the expression (2).

Suppose that as a result of a specific reflectance of the sample 1, the output current Ia representing the light intensity distribution of the images formed on the photodiodes 100b and 100c takes on an asymmetrical distribution characteristic as shown in FIG. 7B. In such a case, the output current Ia1 becomes larger than the output current Ia2 reflecting the quantities of light detected by the photodiodes 100b and 100c. In FIG. 7B, the axis of abscissa stands for positions in the direction X1 on the photodiode 100, and the axis of ordinate represents the output current Ia of the photodiode 100.

Without light branching means 80a, this embodiment would generate a focus detection error with the value z other than 0 in the expression (2). Where the reflectance of the images of the sample 1 formed on the photodiodes 100 and 110 varies in an irregular manner, the focus detection error also changes arbitrarily. Meanwhile, with the light branching means 80a in use by this embodiment, asymmetrical output currents result from the photodiodes 100a, 100b on the one hand and from the photodiodes 110a, 110b on the other hand representing the light intensity distributions of the images formed on the diodes. The distribution asymmetry, as evidenced by distribution characteristics 303 and 305 in FIGS. 7B and 7C, is attributed to the reflectance of the sample 1. In FIG. 7C, the axis of abscissa stands for positions in the direction X2 on the photodiode 110, and the axis of ordinate denotes the output current Ib of the photodiode 110.

Suppose that Ia1 and Ia2 represent intercepted light-derived output currents from the photodiodes 100b and 100c and that Ib1 and Ib2 denote intercepted light-derived output currents from the photodiodes 110b and 110c. In that case, if the sample 1 is at the focal point of the focus detection optics 115b, the value z becomes 0 in the following expressions (3) and (4) with no error detection error perceived regardless of the reflectance irregularity of the sample 1:

$$z=(Ia1 \cdot Ib2 - Ia2 \cdot Ib1)/(Ia1 \cdot Ib2 + Ia2 \cdot Ib1) \quad (3)$$

$$z=(Ia1+Ib2-Ia2-Ib1)/(Ia1+Ib2+Ia2+Ib1) \quad (4)$$

Calculations of the expressions (3) and (4) above provide an outcome showing a substantially reduced noise level thanks to the use of the outputs from the photodiodes 100 and 110, whereby an automatic focusing capability is implemented in a stable manner. The levels of focus detection sensitivity are equivalent to those shown in FIGS. 1C through 1E. The expressions (2), (3) and (4) are furnished as fractional expressions so that the quantity of focus detecting light may be normalized for improved focus detection linearity.

Figure 8A:
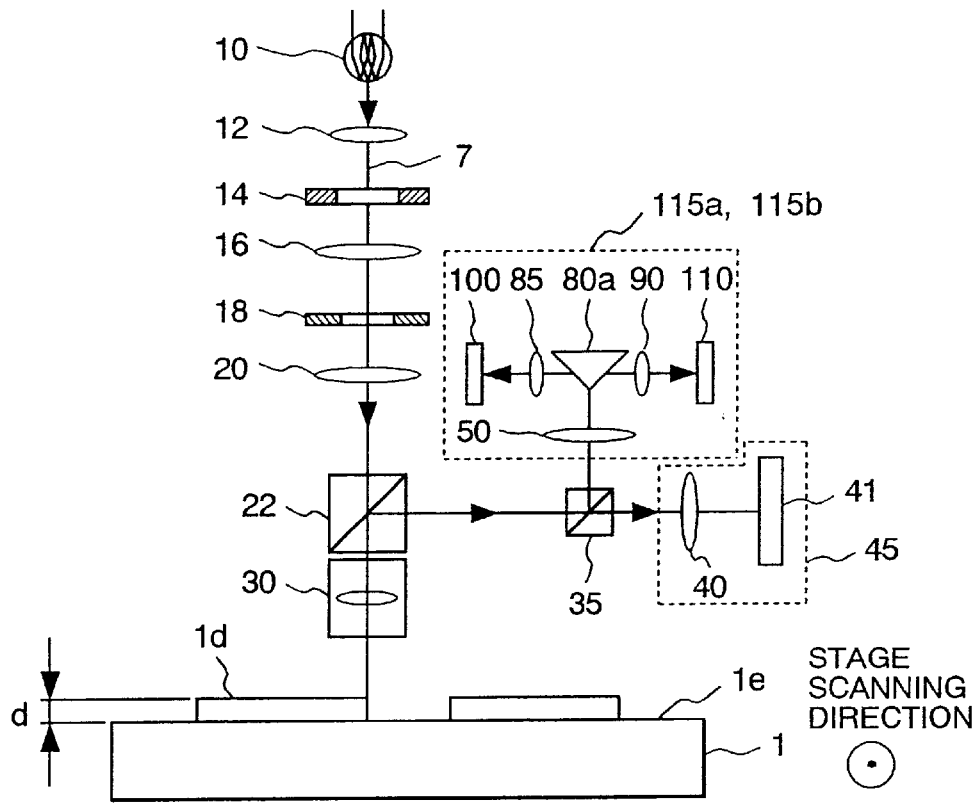
FIG. 8A is a schematic view of optics.
Figure 8B:
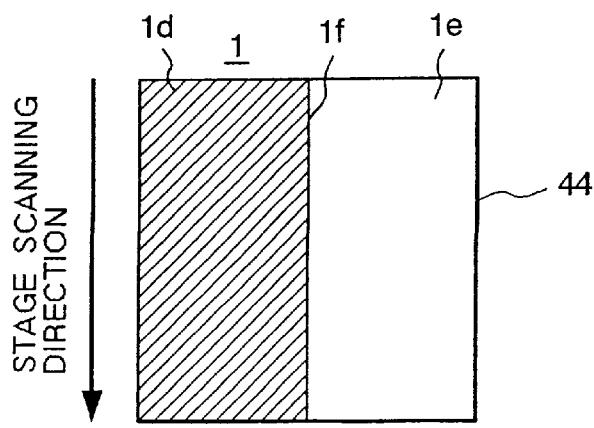
FIG. 8B is a plan view of an image formed on a photoelectric conversion device.

Described below with reference to FIGS. 8A and 8B are reasons why samples with a staggered surface cause focus detection errors to occur. FIG. 8A is a schematic view of optics, and FIG. 8B is a plan view of an image formed on a photoelectric conversion device.

Suppose that a pattern 1d has been formed on the sample 1 and that the pattern 1d has a film thickness "d," as shown in FIGS. 8A and 8B. In that case, if a visual field of the focus detection optics 115a or 115b is located on a boundary dividing staggered surface portions, it is necessary to find where the detected focal point is in terms of height between the pattern 1d and its substrate 1e. For that purpose, the stage 5 is moved at constant speed to let the photoelectric conversion device 41 (i.e., linear image sensor) of the focus detection optics detect an image of the sample surface. The image detected by the sensor is highly likely to be defocused. FIG. 8B shows an image 44 detected by the photoelectric conversion device 41. Illustratively, if the center of the field of the focus detection optics 115a or 115b coincides with the boundary 1f of the pattern stagger, the detected focal point is at an averaged height between the pattern 1d and its substrate 1e. If the film thickness d is substantially greater than the depth of focus (DOF) of the objective lens 30, the images of both the pattern 1d and its substrate 1e are defocused resulting in low levels of detected image quality.

In such cases as the above, the focus detection optics 115a or 115b may detect a plurality of focuses in its field for focus detection. Any one of the detected focuses may be used selectively for focusing with the target surface area on the sample 1, whereby a focused image of the target sample surface is obtained. How the focusing is achieved will be described below in more detail with reference to FIGS. 9A and 9B.

Figure 9A:
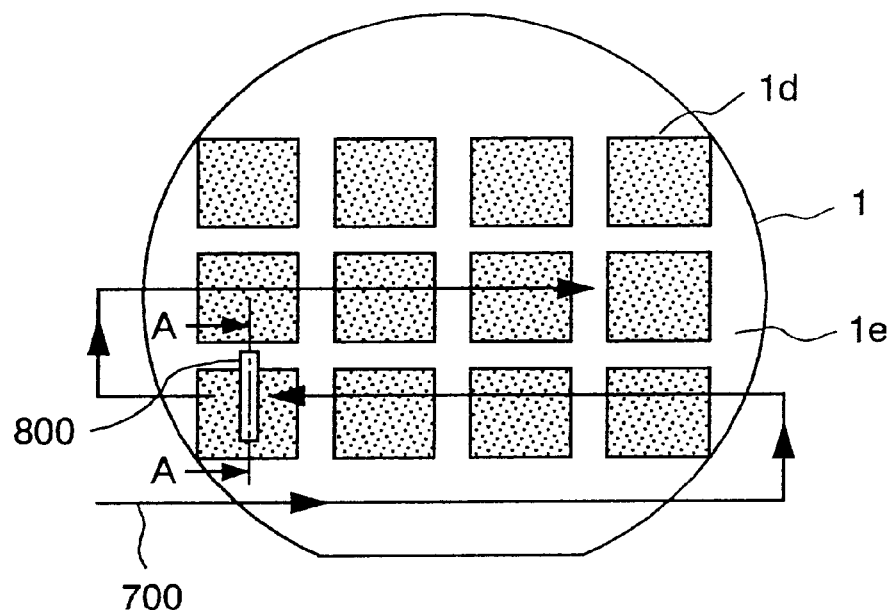
FIG. 9A is a plan view of a sample.
Figure 9B:
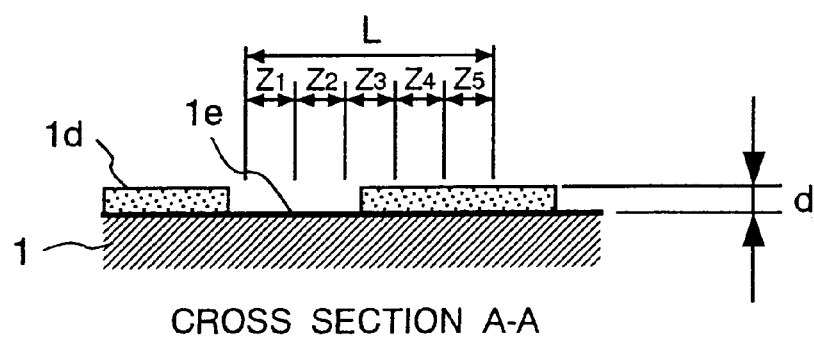
FIG. 9B is a cross-sectional view taken on line A—A in FIG. 9A.

FIG. 9A is a plan view of a sample, and FIG. 9B is a cross-sectional view taken on line A—A in FIG. 9A. As shown in FIG. 9A, the sample 1 is covered with a pattern 1d having a film thickness of "d." The sample 1 is moved in an arrowed direction 700. It is assumed that the field of the image detection optics 45 coincides with the field of the focus detection optics 115. If it is desired to detect the pattern 1d of the entire surface of the sample 1, the focus detection signal processing circuit 120 divides illustratively into five segments the length L of the field 800 of the focus detection optics 115. The height of each of the five zones Z1 through Z5 is acquired. The detected height of the zones Z1 and Z2 represents the height of the pattern substrate 1e, and the detected height of the zone Z3 denotes a height between the pattern 1e and its substrate 1d. The zones Z4 and Z5 when their height is detected stand for the height of the pattern 1d. Using the height thus acquired of the zone Z4 or Z5, the focus detection signal processing circuit 120 prompts the stage controller 150 to control the Z stage 4 via the CPU 140 to attain focusing. This causes the photoelectric conversion device 41 (e.g., linear image sensor) of the image detection optics 45 to produce a focused image of the pattern 1d. If it is desired to detect an image of the pattern substrate 1e, the focus detection signal processing circuit 120 using the detected height of the zone Z1 or Z2 may prompt the stage controller 150 to control the Z stage 4 via the CPU 140 to achieve focusing. A check by the focus detection signal processing circuit 120 to see if the detected height of the zone Z4 or Z5 represents the height of the pattern 1d is made primarily using coordinates furnished by the CPU 140, i.e., coordinates of the pattern on the sample 1 available from design data stored beforehand in the CPU 140, and position coordinates of the X and Y stages 5 and 6 acquired by the CPU 140 from the stage controller 150. Which of the obtained heights of the zones Z1 through Z5 corresponds to which part of the sample 1 is recognized by the focus detection signal processing circuit 120 comparing the detected heights with the three-dimensional structure of the sample 1 based on the design data about the sample available from the CPU 140.

Described below with reference to FIGS. 10A through 10D is means for obtaining heights of, for example, five points in the field 800 of the focus detection optics 115. FIG. 10A is a schematic view of focus detection optics, and FIGS. 10B through 10D are views indicating intensity levels of light intercepted by photoelectric conversion devices.

In FIG. 10A, focus detecting light is split by the knife-edge type mirror 80a into two beams entering photodiode arrays 100 and 110 each divided into 10 segments. In FIG. 10B, images of the sample 1 formed on the photodiode arrays 100 and 110 as viewed in arrowed directions A and B are shown with light intensity gradations. In FIG. 10C, $I\alpha 1$ through $I\alpha 10$ and $I\beta 1$ through $I\beta 10$ stand for output currents derived from the quantities of light intercepted by the photodiodes 100 and 110. Of these output currents, $I\alpha 1$ through $I\alpha 6$ and $I\beta 1$ through $I\beta 6$ manifest themselves asymmetrical in distribution characteristics between the opposed photodiode zones, e.g., $I\alpha 1$ versus $I\alpha 2$. The asymmetry is attributed to reflectance irregularities of the sample 1.

In the case above, the focus detection signal processing circuit 120 substitutes $I\alpha 1+I\beta 2$ for $I\gamma 1$, and $I\alpha 2 + I\beta 1$ for $I\gamma 2$ in their respective zones. When the light intensities of $I\alpha 1$ and $I\alpha 2$ are obtained through comparison by the focus detection signal processing circuit 120 having performed first focus detection, typical results of which are shown in FIG. 10D, it is possible to forestall waveform asymmetry stemming from reflectance irregularities and thereby to eliminate focus detection errors. The focus detection signal processing circuit 120 may carry out the same process on $I\alpha 3$ through $I\alpha 10$ and $I\beta 3$ through $I\beta 10$ to obtain the remaining four focuses. Specifically, the processing circuit 120 may substitute $I\alpha3+I\beta4$ for $I\gamma3$, $I\alpha4+I\beta3$ for $I\gamma4$, $I\alpha5+I\beta6$ for $I\gamma5$, $I\alpha6+I\beta5$ for $I\gamma6$, $I\alpha7+IP8$ for $I\gamma7$, $I\alpha8+I\beta7$ for $I\gamma8$, $I\alpha9+I\beta10$ for $I\gamma9$, and $I\alpha10+I\beta9$ for $I\gamma10$ for the respective zones. In order to detect heights at a plurality of points on the sample, the photoelectric conversion devices 100 and 110 of the focus detection optics 115 may also be a two-dimensionally arranged photodiode array or a TV camera each. This embodiment performs automatic focusing of a staggered-surface sample by acquiring a plurality of focuses in the focus detecting field and by selectively subjecting detected heights of the staggered surface zones to the focusing process. This makes it possible stably to detect focused images of the target sample.

Figure 11:
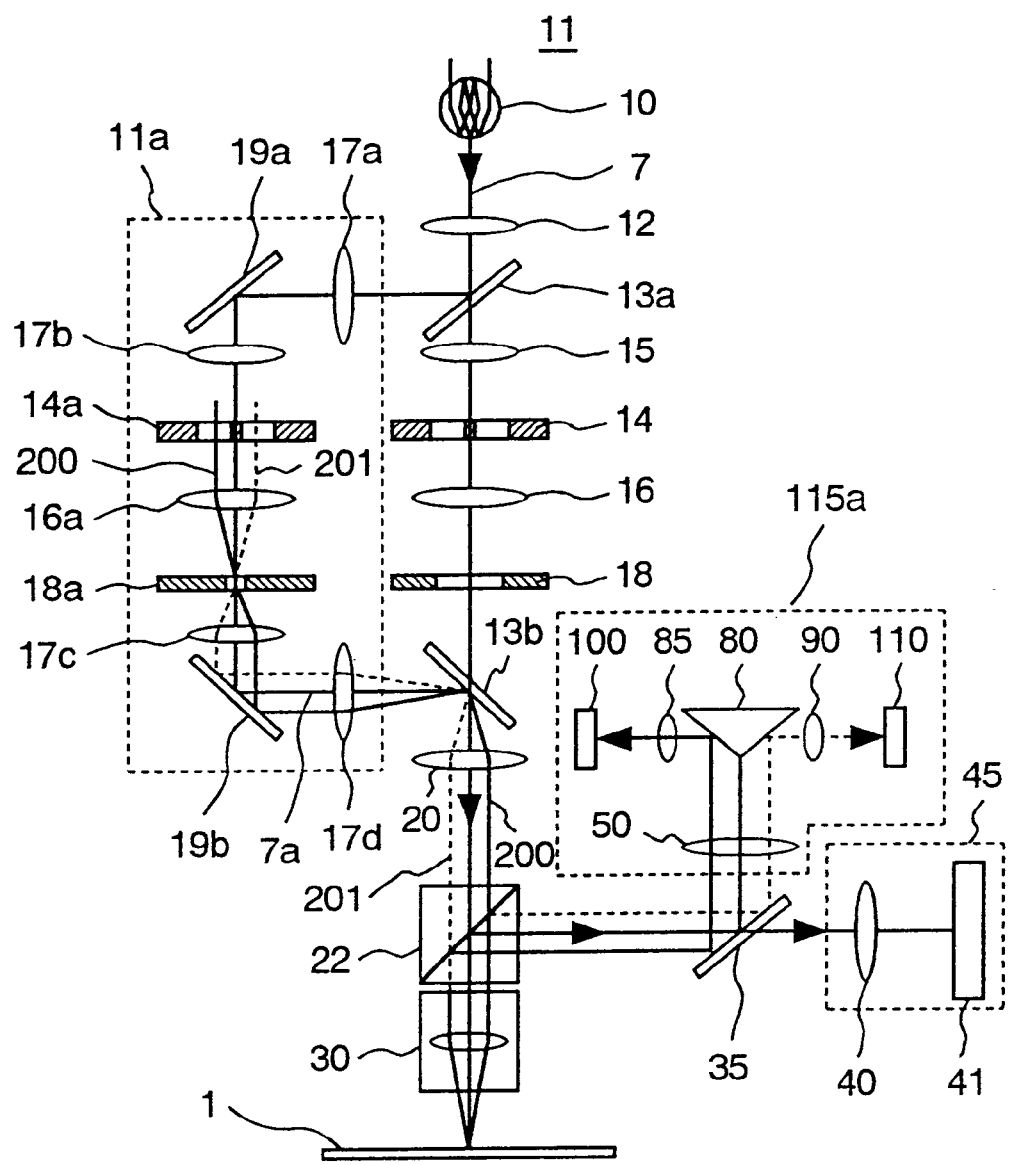
FIG. 11 is a schematic view of illumination optics and focus detection optics also embodying the invention and used by the visual inspection apparatus of FIG. 5.

Described below with reference to FIG. 11 is a setup wherein an illuminating system for the image detection optics 45 for the sample 1 is separated from an illuminating system for the focus detection optics 115. FIG. 11 is a schematic view of illumination optics and focus detection optics also embodying the invention and used by the visual inspection apparatus of FIG. 5.

The focus detection optics 115a and image detection optics 45 in FIG. 11 are identical to their counterparts shown in FIG. 5. Whereas the illumination optics 11 in FIG. 5 has only one optical path, the illumination optics 11 for image detection in FIG. 11 uses short wavelength light as shown in FIG. 4A, and the illumination optics 11a for focus detection utilizes long wavelength light. Thus the dichroic mirror 13 of the illumination optics 11 has transmittance T with a characteristic shown in FIG. 4B.

The aperture stop 14a used by the illumination optics 11a for focus detection shown in FIGS. 4A and 11 will now be described with reference to FIGS. 12A through 12D.

FIGS. 12A through 12D are plan views of aperture stops. Generally, the aperture stop 14a is implemented as one 114a with a round opening 14d shown in FIG. 12A. It is known that the greater the incident angle of the illuminating light for focus detection with respect to the sample 1, the higher the level of focus detecting sensitivity. For that reason, as shown in FIG. 12B, there is a common practice of shading that part of the light beam which is close to the optical axis of an aperture stop 114b and which has a small incident angle relative to the sample surface. In this case, openings 14e and 14f are provided away from the optical axis so as to gain higher optical sensitivity than the aperture stop 114a of FIG. 12A. It is assumed that the illumination optics 11a provides Koehler illumination. The quantity of focus detecting light is effectively maximized, as shown in FIG. 12C, by furnishing an aperture stop 114c having openings 14g and 14h shaped to be in conjugate relation to the pupil of the objective lens 30 while the vicinity of the optical axis prone to low focus detection sensitivity is shaded. If a plurality of objective lenses 30 are used by turns, the size of the openings 14g and 14h may be determined with the largest of the different pupil diameters taken into consideration. This will make it unnecessary to replace the aperture stop 14a every time a different objective lens 30 is mounted. It should be noted that an aperture stop 14a with an opening size larger than the pupil diameter of the objective lens 30 will increase the quantity of stray light reaching the photoelectric conversion devices 100 and 110. In such a case, it is desirable to prepare an aperture stop 114d having openings 14i and 14j (see FIG. 12D) with a size different from that of the openings 14g and 14h of the aperture stop 114c, so that the aperture stop 14a may be replaced at the same time as the objective lens 30. In the aperture stops 114b through 114d described above, the direction in which the sample 1 is illuminated is that in which the openings 14e through 14j are opposed. The light transmitted through the openings 14e, 14g and 14i is led to the photoelectric conversion device 100 of the focus detection optics 115, and the light having passed through the openings 14f, 14h and 14j is guided to the photoelectric conversion device 110 of the focus detection optics 115.

The field stop 18a used in the setups of FIGS. 4A and 11 will now be described with reference to FIGS. 13A and 13B.

FIGS. 13A and 13B are plan views of field stops. The field stop 18a may be implemented illustratively as a field stop 118a having a slit 18b with a narrow width in the direction of focus detection, as shown in FIG. 13A. That is, the width of the slit 18b represents the direction of focus detection. The length of the slit 18b need not be perpendicular to the direction of focus detection. More specifically, the lengthwise direction of the slit 18b need only have an angle of at least 45 degrees with respect to the direction of focus detection. Alternatively, as shown in FIG. 13B, there may be provided a field stop 118b having a plurality of slit openings 18c. With the field stop 118b in use, the center of each of the slits is acquired using a pair of photoelectric conversion devices, whereby any focus detection error is minimized. Where the field stop 118b of FIG. 13B is employed, it is necessary to use two-dimensional sensors such as TV cameras.

Figure 14:
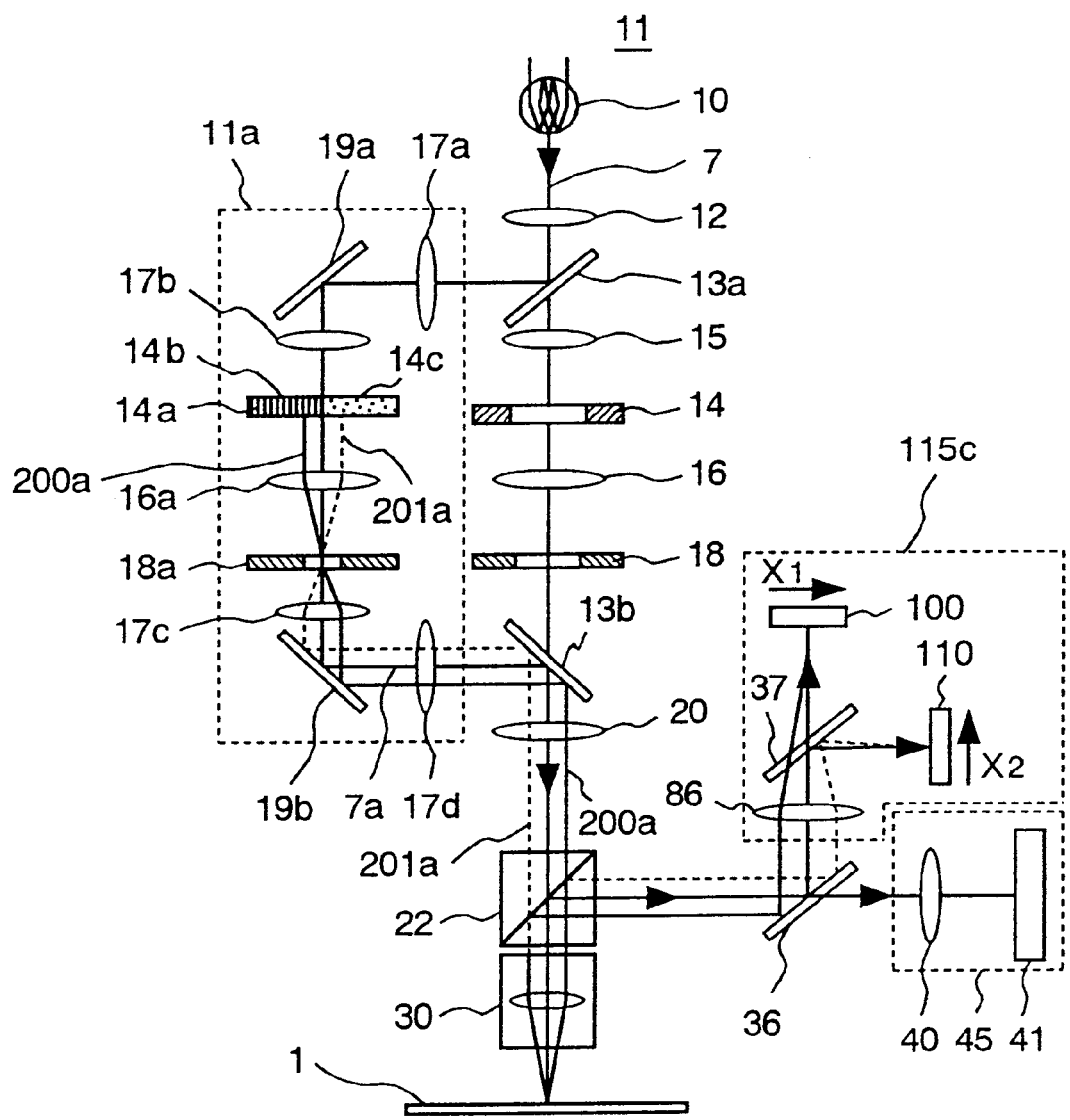
FIG. 14 is a schematic view of illumination optics and focus detection optics also embodying the invention.

FIG. 14 is a schematic view of illumination optics and focus detection optics also embodying the invention. Described below with reference to FIG. 14 are further examples of the focus detecting illumination optics 11a and the focus detection optics 115c. This embodiment utilizes a dichroic mirror 37 as light branching means for the focus detection optics 115c. Light reflected by the dichroic mirror 13a in the illumination optical path proceeds to the focus detecting illumination optics 11a, reaching the aperture stop 14a. The aperture stop 14a is furnished with films 14b and 14c having two spectral transmission factors in the direction of the light illuminating the sample 1. The film 14b is a short wavelength transmission film through which a short wavelength half of the light beam led to the focus detecting illumination optics 11a is transmitted. The film 14c is a long wavelength transmission film through which a long wavelength half of the same light beam led to the optics 11a is transmitted. The short wavelength transmission film 14b is attached to the openings 14e, 14g and 14i shown in FIG. 12B through 12D, while the long wavelength transmission film 14c is fixed to the openings 14f, 14h and 14j in the same figures. Short wavelength light 200a and long wavelength light 201a having passed through the aperture stop 14a are transmitted through the field stop 18a. The two light beams are reflected by the dichroic mirror 13b via the mirror 19b and lens 17d to join the illuminating light for image detection coming from the illumination optics 11. The combined light beams are condensed by the objective lens 30 and irradiated to the sample 1. Reflected light from the sample 1 enters the objective lens 30 and is again reflected by the light branching means 22.

Of the reflected light, that wavelength part which comes from the focus detecting illumination optics 11a is reflected by the dichroic mirror 36, and the wavelength part from the illumination optics 11 passes through the dichroic mirror 36. The dichroic mirror 36 needs to have the same spectral transmission factor as the dichroic mirror 13a of the illumination optics 11. The light beam entering the focus detecting illumination optics 115c is allowed to have its short wavelength half transmitted through the dichroic mirror 37 of the optics 115c, thus forming an image of the sample 1 on the photoelectric conversion device 100. The long wavelength half of the light beam is reflected by the dichroic mirror 37, forming an image of the sample 1 on the photoelectric conversion device 110. With this embodiment, where a high reflectance region and a low reflectance region coexist on the sample 1, the short wavelength illuminating light 200a emitted from the objective lens 30 to the sample 1 diagonally with respect to the optical axis is intercepted by the photoelectric conversion device 100. This allows the current distribution characteristic 306 shown in FIG. 6B to be detected depending on the intensity distribution of the light emitted to the photoelectric conversion device 100. In addition, the photoelectric conversion device 110 intercepts the long wavelength illuminating light 201a emitted from the objective lens 30 to the sample 1 symmetrically about the optical axis and diagonally relative to the illuminating light 200a. This allows the current distribution characteristic 307 shown in FIG. 6C to be detected. The current distribution characteristics 306 and 307 representing the light intensity distribution of the images formed on the photoelectric conversion devices 100 and 110 are each asymmetrical, reflecting the sample surface reflectance distribution. If the sample surface 1a is at the focal point of the focus detection optics 115c, the current distribution characteristic 306 detected by the photoelectric conversion device 100 becomes the same as the characteristic 307 detected by the device 110. This makes it possible for the focus detection signal processing circuit 120 to obtain the current distribution characteristic 308 of FIG. 6D. The distribution characteristic 308 is obtained by adding up the characteristics 306 and 307 symmetrically about the reference optical axis 7. Thus the distribution characteristic 308 takes a symmetrical waveform about the optical axis and has no focus detection error dependent on the reflectance distribution of the sample surface 1a, whereby highly precise focus detection is implemented.

Preferably, the focus detection optics 115c may include an optical system for rotating an image by 180 degrees between the dichroic mirror 37 on the one hand and the photoelectric conversion device 100 or 110 on the other hand, and an optical system for composing the resulting images into a composite image on the photoelectric conversion device 100. The device 100 acting as a sensor may then provide the distribution characteristic 308 of FIG. 6D.

Figure 15:
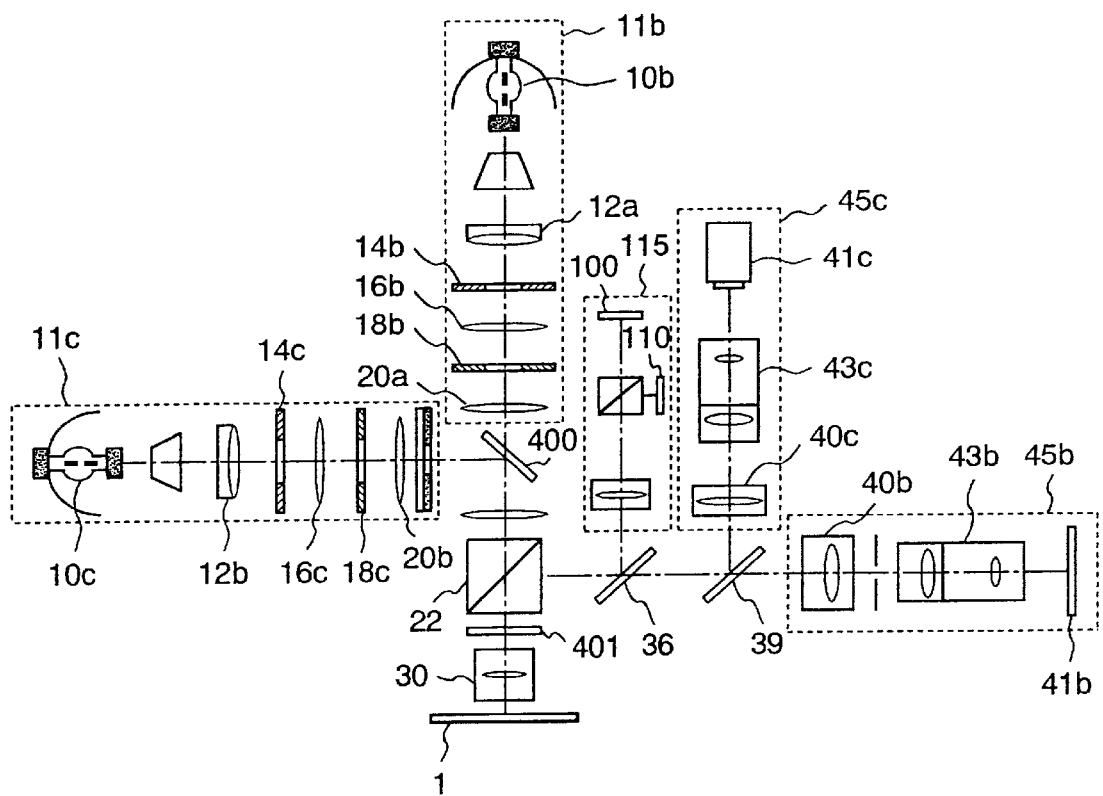
FIG. 15 is a schematic view of illumination optics and focus detection optics also embodying the invention.

The illumination optics 11 has so far been shown using a single light source. Described below with reference to FIG. 15 is illumination optics employing a plurality of light sources. FIG. 15 is a schematic view of illumination optics and focus detection optics also embodying the invention.

In FIG. 15, the main illumination optics comprises ultraviolet illumination optics 11b and visible light illumination optics 11c. The detection optics includes ultraviolet detection optics 45b, visible light detection optics 45c, and focus detection optics 115. The ultraviolet illumination optics 11b is provided to emit ultraviolet rays of short wavelengths to the sample 1. This makes it possible for the image detecting illumination optics 45 to detect micro-patterns 0.4 $\mu$m or less in size (0.4 $\mu$m, 0.2 $\mu$m, 0.1 $\mu$m) on the sample 1 by enhancing the resolving power to form the micro-pattern images.

The ultraviolet illumination optics 11b has a light source 10b (e.g., Hg—Xe lamp) that emits ultraviolet rays passing through a lens 12a, an aperture stop 14b, a lens 16b, a field stop 18b, a lens 20a and a dichroic mirror 400. The illuminating ultraviolet light is transmitted through a polarized beam splitter 22 and a ¼ waveform plate 401, constituting a circularly polarized light component. This light component passes through the objective lens 30 to light the sample 1 with Koehler illumination. After being reflected and diffracted by the sample 1, the light again enters the objective lens 30, passes through the ¼ wavelength plate and is reflected by the polarized beam splitter 22. After transmission through the dichroic mirrors 36 and 39, the ultraviolet light enters an imaging lens 40b of the ultraviolet detection optics 45b, whereby an ultraviolet-based image of the pattern on the sample 1 is formed. The image is magnified by a zoom lens 43b and projected onto a sensor 41b. Where ultraviolet rays with their small angles of diffraction are used for a light source as described, the sensor 41b can pick up the sample 1 to form a high-resolution image of its micro-patterns 0.4 $\mu$m or less in size such as those of semiconductor wafers.

The visible light illumination optics 11c has a visible light source 10c that emits visible light passing through a lens 12b, an aperture stop 14c, a lens 16c, a field stop 18c, and a lens 20b to reach the dichroic mirror 400. After being reflected by the dichroic mirror 400, the visible light passes through the polarized beam splitter 22, ¼ wavelength plate 401 and objective lens 30 to light the sample 1 with Koehler illumination. After being reflected and diffracted by the sample 1, the light again enters the objective lens 30, passes through the ¼ wavelength plate and is reflected by the polarized beam splitter 22. Part of the visible light is reflected by the dichroic mirror 36 to reach the focus detection optics 115, forming images on the photoelectric conversion devices 100 and 110 for focus detection. That part of the visible light which passes through the dichroic mirror 36 and is reflected by the dichroic mirror 39 enters an imaging lens 40c of the visible light detection optics 45c, forming a visible light-based image of the pattern on the sample 1. The image thus formed is magnified by a zoom lens 43c and projected onto a sensor 41c.

The purpose of magnifying the image by the zoom lens 43c for projection onto the sensor 41c is to convert the pixel size on the sensor 41c in a way that matches the pixel size on the sample 1, whereby images of micro-patterns (0.2 $\mu$m×0.2 $\mu$m or less in size) on the sample 1 may be formed. Although the visible light illumination optics 11c above was shown using the same visible light illumination for both image detection and focus detection, this is not limitative of the invention. An obvious alternative involves, as shown in FIGS. 4A and 11, setting up visible light optics for image detection separately from and in parallel with visible light optics for focus detection. Such a dual optics structure makes it possible to establish settings for the field stop 18 and aperture stop 14 to address both focus detection and image detection more appropriately.

Because the embodiment of FIG. 15 detects images of the sample 1 using ultraviolet rays and visible light, it is possible to implement an image and focus detection scheme dealing suitably with infinitesimal patterns formed on the sample 1. The focus detection optics 115 may alternatively be provided in two separate units, one utilizing ultraviolet rays, the other employing visible light.

Some semiconductor wafers have thin films formed thereon. Conventional optics have experienced focus detection errors attributable to light interference caused by the presence of such thin films on the wafer surface. By contrast, the inventive apparatus forestalls such errors in the manner described and provides a highly accurate focus detection capability.

As described, embodiments of the invention carry out automatic focusing of the surface of samples such as semiconductor wafers known to bear infinitesimal surface patterns with their reflectance factors subtly changed, so that microscopic defects including foreign matters may be inspected at high levels of resolution.

The inventive focus detection method and apparatus prevent focus detection errors caused by asymmetrical intensity distribution characteristics of the light used for focus detection, the asymmetry being attributable to reflectance irregularities on the sample. According to the invention, a simplified constitution of the focus detection apparatus still ensures highly accurate focus detection.

The invention may be embodied in other specific forms without departing from the spirit or essential characteristics thereof. The present embodiments are therefore to be considered in all aspects as illustrative and not restrictive, the scope of the invention being indicated by the appended claims rather than by the foregoing description and all changes which come within the meaning and range of equivalency of the claims are therefore intended to be embraced therein.

What is claimed is:

1. An automatic focus detection method comprising the steps of:

irradiating onto a single spot of a sample a plurality of beams of illuminating light transmitted and condensed through an objective lens in a symmetrically diagonal manner with respect to an optical axis of said objective lens;

branching reflected light from the same spot of the illuminated sample after transmission through said objective lens, in the directions of said beams of illuminating light;

irradiating an optical image formed by a branch of said reflected light onto a photoelectric conversion device for conversion to an electric signal representing intensity distribution of the irradiated optical image; and detecting a defocus of said sample based on a discrepancy between said optical axis and the center of the light intensity distribution on said photoelectric conversion device.

2. An automatic focus detection method according to claim 1, further comprising the steps of:

producing a mirror image of one optical image formed by one branch of said reflected light in inverse relation to another optical image formed by another branch of said reflected light; and composing said mirror image and said another optical image formed by said another branch of said reflected light so as to form a composite image which is irradiated onto said photoelectric conversion device.

3. An automatic focus detection method according to claim 1, further comprising the step of irradiating each of a plurality of optical images formed by branches of said reflected light onto each of different photoelectric conversion devices.

4. An automatic focus detection method according to claim 3, further comprising the step of detecting defocuses at a plurality of points on said sample.

5. An automatic focus detection method comprising the steps of:

irradiating onto a single spot of a sample a plurality of beams of illuminating light transmitted and condensed through an objective lens in a symmetrically diagonal manner with respect to an optical axis of said objective lens;

branching reflected light from the same spot of the illuminated sample after transmission through said objective lens, in the directions of said beams of illuminating light;

producing a mirror image of one optical image formed by one branch of said reflected light in inverse relation to another optical image formed by another branch of said reflected light;

composing said mirror image and said another optical image formed by said another branch of said reflected light so as to form a composite image which is irradiated onto said photoelectric conversion device for conversion to an electric signal representing intensity distribution of the irradiated optical image; and detecting a defocus of said sample based on a discrepancy between said optical axis and the center of the light intensity distribution on said photoelectric conversion device.

6. An automatic focus detection method according to claim 5, wherein said irradiating step comprises irradiating a major portion of said illuminating light.

7. An automatic focus detection method according to claim 5, wherein said branching step includes the step of branching said reflected light in directions of illumination symmetrical with respect to said optical axis.

8. An automatic focus detection method according to claim 5, wherein said branching step is carried out by use of a first and a second optical path having mirrors each, the number of mirrors of said second optical path being different from the number of mirrors of said first optical path by an odd number.

9. An automatic focus detection method according to claim 5, wherein said photoelectric conversion device is a photoelectric transducer.

10. An automatic focus detection method comprising the steps of:

irradiating onto a single spot of a sample a plurality of beams of illuminating light transmitted and condensed through an objective lens in a symmetrically diagonal manner with respect to an optical axis of said objective lens;

branching reflected light from the same spot of the illuminated sample after transmission through said objective lens, in directions of illumination symmetrical with respect to said optical axis;

irradiating each of a plurality of optical images formed by branches of said reflected light onto each of different photoelectric conversion devices for conversion to electric signals representing intensity distribution of the irradiated optical images;

processing said electric signals obtained from said photoelectric conversion devices; and detecting a defocus of said sample by use of the processed electric signals representing a discrepancy between said optical axis and the center of the light intensity distribution of each irradiated optical image.

11. An automatic focus detection method according to claim 10, further comprising the step of processing said electric signals obtained from said photoelectric conversion devices so that light intensity distribution levels of the irradiated optical images become symmetrical with respect to said optical axis.

12. An automatic focus detection method according to claim 10, further comprising the step of obtaining defocuses of said sample at a plurality of proximate points thereon.

13. An automatic focus detection apparatus comprising:

illumination optics for irradiating onto a single spot of a sample a plurality of beams of illuminating light transmitted and condensed through an objective lens in a symmetrically diagonal manner with respect to an optical axis of said objective lens; and focus detection optics including a branching optical element for branching reflected light from the same spot of the illuminated sample after transmission through said objective lens, in directions of illumination symmetrical with respect to said optical axis so as to obtain a plurality of optical images; and a photoelectric conversion device for receiving the optical images from said branching optical element and converting the received images into signals representing light intensity distribution levels of the images.

14. An automatic focus detection apparatus according to claim 13, wherein said photoelectric conversion device receives a composite image made of optical images which are branched by said branching optical element and are in inverse relation to one another.

15. An automatic focus detection apparatus according to claim 13, wherein said photoelectric conversion device receives optical images branched by said branching optical element.

16. An automatic focus detection apparatus comprising:
illumination optics for irradiating onto a single spot of a sample a plurality of beams of illuminating light transmitted and condensed through an objective lens in a symmetrically diagonal manner with respect to an optical axis of said objective lens; and focus detection optics including a branching optical element for branching reflected light from the same spot of the illuminated sample after transmission through said objective lens, in directions of illumination symmetrical with respect to said optical axis so as to obtain a plurality of optical images; inversion optics for producing a mirror image of one optical image formed by one branch of said reflected light in inverse relation to another optical image formed by another branch of said reflected light; composition optics for composing said mirror image and said another optical image so as to form a composite image; and a photoelectric conversion device for receiving said composite image formed by said composition optics and converting the received image into a signal representing light intensity distribution of the image.

17. An automatic focus detection apparatus according to claim 16, wherein said illumination optics includes an aperture stop and a field stop, said field stop being used to irradiate a slit-like beam of light onto said sample.

18. An automatic focus detection apparatus according to claim 16, wherein said branching optical element has a knife-edge type mirror for branching said reflected light.

19. An automatic focus detection apparatus according to claim 16, wherein said inversion optics has a first and a second optical path having mirrors each, the number of mirrors of said second optical path being different from the number of mirrors of said first optical path by an odd number.

20. An automatic focus detection apparatus according to claim 16, wherein said photoelectric conversion device outputs an electric signal representing a discrepancy between said optical axis and the center of the light intensity distribution on said photoelectric conversion device.

21. An automatic focus detection apparatus according to claim 16, further comprising means for obtaining defocuses of said sample at a plurality of proximate points thereon.

22. An automatic focus detection apparatus comprising:
illumination optics for irradiating onto a single spot of a sample a plurality of beams of illuminating light transmitted and condensed through an objective lens in a symmetrically diagonal manner with respect to an optical axis of said objective lens;

focus detection optics including a branching optical element for branching reflected light from the same spot of the illuminated sample after transmission through said objective lens, in directions of illumination symmetrical with respect to said optical axis so as to obtain a plurality of optical images; imaging optics for forming said plurality of optical images branched by said branching optical element; and a plurality of photoelectric conversion devices for receiving said optical images formed by said imaging optics and converting the received images into signals representing light intensity distribution levels of the images; and a processing circuit for symmetrically processing said signals representing the light intensity distribution levels on said photoelectric conversion devices.

23. An automatic focus detection apparatus according to claim 22, wherein said illumination optics includes an aperture stop and a field stop, said field stop being used to irradiate a slit-like beam of light onto said sample.

24. An automatic focus detection apparatus according to claim 22, wherein said branching optical element has a knife-edge type mirror for branching said reflected light.

25. An automatic focus detection apparatus according to claim 22, further comprising means for detecting a defocus of said sample based on a discrepancy between said optical axis and the center of the light intensity distribution obtained from said processing circuit.

26. An automatic focus detection apparatus according to claim 22, further comprising means for obtaining defocuses of said sample at a plurality of proximate points thereon.

27. An inspection apparatus comprising:
illumination optics for illuminating a sample from above through an objective lens;

branching optics for capturing through said objective lens reflected light from said sample under illumination by said illumination optics so as to branch the captured reflected light;

image detection optics including a first photoelectric conversion device, said image detection optics forming a pattern image based on the branched reflected light from said branching optics, said pattern image being received by said first photoelectric conversion device for conversion into an image signal to be detected;

focus detection optics including a branching optical element for branching the light branched by said branching optics, in directions of illumination symmetrical with respect to the optical axis of the illuminating light irradiated to said sample; and a second photoelectric conversion device for receiving an optical image based on the branched light from said branching optical element and converting the image into a focus detection signal to be output; and a processing circuit for processing the output of said second photoelectric conversion device.

28. An inspection apparatus comprising:
illumination optics for illuminating a sample from above through an objective lens;

branching optics for capturing through said objective lens reflected light from said sample under illumination by said illumination optics so as to branch the captured reflected light;

image detection optics including a first photoelectric conversion device, said image detection optics forming an image based on the branched reflected light from said branching optics, said image being received by said first photoelectric conversion device for conversion into an image signal to be detected; and focus detection optics including a branching optical element for branching the light branched by said branching optics, into a plurality of optical paths in directions symmetrical with respect to the optical axis of the illuminating light irradiated to said sample; inversion optics for producing a mirror image of one optical image formed by one branch of said reflected light in inverse relation to another optical image formed by another branch of said reflected light; composition optics for composing said mirror image and said another optical image so as to form a composite image; and a second photoelectric conversion device for receiving said composite image formed by said composition optics and converting the received image into a focus detection signal to be output.

29. An inspection apparatus according to claim 28, wherein said objective lens is made of a lens corrected substantially at infinity, and wherein said branching optical element is constituted by a knife-edge type mirror interposed between said objective lens and said composition optics.

30. An inspection apparatus comprising:

illumination optics for illuminating a sample from above through an objective lens by use of illuminating light for image detection and illuminating light for focus detection;

branching optics for capturing through said objective lens reflected light from said sample under illumination by said illumination optics so as to branch the captured reflected light;

image detection optics including a first photoelectric conversion device, said image detection optics forming an image based on the reflected illuminating light for image detection branched by said branching optics, said image being received by said first photoelectric conversion device for conversion into an image signal;

focus detection optics including a branching optical element for branching the light branched by said branching optics, into a plurality of optical paths in directions symmetrical with respect to the optical axis of said illuminating light for focus detection irradiated to said sample; inversion optics for producing a mirror image of one optical image formed by one branch of said reflected light in inverse relation to another optical image formed by another branch of said reflected light; composition optics for composing said mirror image and said another optical image so as to form a composite image; and a second photoelectric conversion device for receiving said composite image formed by said composition optics and converting the received image into a focus detection signal to be output;

focus controlling means for controlling focusing on said sample on the basis of said focus detection signal from said focus detection optics; and image processing means for inspecting status of patterns formed on said sample on the basis of said image signal from said image detection optics.

31. An inspection apparatus according to claim 30, wherein said illumination optics includes means for irradiating onto said sample ring-like illuminating light as said illuminating light for image detection.

32. An inspection apparatus according to claim 30, wherein said illumination optics includes a first illuminating path for permitting transmission of said illuminating light for image detection having a first wavelength; a second illuminating path for permitting transmission of said illuminating light for focus detection having a second wavelength; and composing means for composing said illuminating light for image detection and said illuminating light for focus detection.

33. An inspection apparatus according to claim 30, wherein said illumination optics includes ultraviolet light illumination optics for emitting ultraviolet light for image detection; visible light illumination optics for emitting visible light for focus detection; and composing means for composing said ultraviolet light and said visible light.

34. An inspection apparatus according to claim 30, wherein said illumination optics includes a stop whereby said illuminating light for focus detection is irradiated as a slit-like beam of light onto said sample.

35. An inspection apparatus according to claim 30, wherein said objective lens is made of a lens corrected substantially at infinity, and wherein said branching optical element is constituted by a knife-edge type mirror interposed between said objective lens and said composition optics.

36. An inspection apparatus comprising:

illumination optics for illuminating a sample from above through an objective lens;

branching optics for capturing through said objective lens reflected light from said sample under illumination by said illumination optics so as to branch the captured reflected light;

image detection optics including a first photoelectric conversion device, said image detection optics forming an image based on the branched reflected light from said branching optics, said image being received by said first photoelectric conversion device for conversion into an image signal to be detected;

focus detection optics including a branching optical element for branching the light branched by said branching optics, into a plurality of optical paths in directions symmetrical with respect to the optical axis of the illuminating light irradiated to said sample; imaging optics for forming said plurality of optical images branched by said branching optical element; and a plurality of second photoelectric conversion devices for receiving said optical images formed by said imaging optics and converting the received images into signals representing light intensity distribution levels of the images;

a processing circuit for outputting a focus detection signal by carrying out processing so that said signals output by said second photoelectric conversion devices become symmetrical;

focus controlling means for controlling focusing on said sample on the basis of said focus detection signal from said processing circuit; and image processing means for inspecting status of patterns formed on said sample on the basis of said image signal from said image detection optics.

37. An inspection apparatus comprising:

illumination optics for illuminating a sample from above through an objective lens by use of illuminating light for image detection and illuminating light for focus detection;

branching optics for capturing through said objective lens reflected light from said sample under illumination by said illumination optics so as to branch the captured reflected light;

image detection optics including a first photoelectric conversion device, said image detection optics forming an image based on the reflection of one of the two kinds of illuminating light branched by said branching optics, said image being received by said first photoelectric conversion device for conversion into an image signal to be output;

focus detection optics including a branching optical element for branching the other illuminating light branched by said branching optics, into a plurality of optical paths in directions symmetrical with respect to the optical axis of said illuminating light for focus detection irradiated to said sample; imaging optics for forming a plurality of optical images from said plurality of optical paths branched by said branching optical element; and a plurality of second photoelectric conversion devices for receiving said plurality of images formed by said imaging optics from said plurality of optical paths and converting the received images into signals representing light intensity distribution levels of the images;

a processing circuit for outputting a focus detection signal by carrying out processing so that said signals output by said second photoelectric conversion devices become symmetrical;

focus controlling means for controlling focusing on said sample on the basis of said focus detection signal from said processing circuit; and image processing means for inspecting image status on said sample on the basis of said image signal from said image detection optics.

38. An inspection apparatus according to claim 37, wherein said illumination optics includes a stop whereby said illuminating light for focus detection is irradiated as a slit-like beam of light onto said sample.

39. An inspection apparatus according to claim 37, wherein said objective lens is made of a lens corrected substantially at infinity, and wherein said branching optical element is constituted by a knife-edge type mirror interposed between said objective lens and said imaging optics.

40. An inspection apparatus according to claim 37, wherein said illumination optics includes means for irradiating onto said sample ring-like illuminating light as said illuminating light for image detection.

41. An inspection apparatus according to claim 37, wherein said illumination optics includes a first illuminating path for permitting transmission of said illuminating light for image detection having a first wavelength; a second illuminating path for permitting transmission of said illuminating light for focus detection having a second wavelength; and composing means for composing said illuminating light for image detection and said illuminating light for focus detection.

42. An inspection apparatus according to claim 37, wherein said illumination optics includes ultraviolet light illumination optics for emitting ultraviolet light for image detection; visible light illumination optics for emitting visible light for focus detection; and composing means for composing said ultraviolet light and said visible light.

* * * * *